(12) United States Patent
Garzino-Demo et al.

(10) Patent No.: US 7,708,983 B2
(45) Date of Patent: May 4, 2010

(54) DIRECTIONAL INDUCTION OF IMMUNE RESPONSE BY CO-ADMINISTRATION OF ANTIGENS WITH CHEMOKINES

(76) Inventors: Alfredo Garzino-Demo, 4539 Keswick Rd., Baltimore, MD (US) 21210; Robert C. Gallo, 9100 Aldershot Dr., Bethesda, MD (US) 20817; Anthony L. Devico, 5433 Peacock Ave., Alexandria, VA (US) 22304

( * ) Notice: Subject to any disclaimer, the term of this patent is extended or adjusted under 35 U.S.C. 154(b) by 458 days.

(21) Appl. No.: 11/458,555

(22) Filed: Jul. 19, 2006

(65) Prior Publication Data
US 2008/0112976 A1 May 15, 2008

Related U.S. Application Data

(63) Continuation-in-part of application No. 11/072,798, filed on Mar. 4, 2005, now Pat. No. 7,384,641.

(60) Provisional application No. 60/700,690, filed on Jul. 19, 2005.

(51) Int. Cl.
*A61K 38/19* (2006.01)
*A61K 39/21* (2006.01)
*C12N 15/00* (2006.01)

(52) U.S. Cl. ............ 424/85.1; 424/208.1; 514/44; 435/320.1

(58) Field of Classification Search ............ None
See application file for complete search history.

(56) References Cited

U.S. PATENT DOCUMENTS

| | | | |
|---|---|---|---|
| 5,141,867 | A | 8/1992 | Ivanoff et al. |
| 6,569,418 | B1 | 5/2003 | Garzino Demo et al. |
| 6,919,318 | B1 | 7/2005 | Paliard |
| 6,919,319 | B2 | 7/2005 | Garzino Demo et al. |
| 2005/0208017 | A1 | 9/2005 | Garzino Demo et al. |

FOREIGN PATENT DOCUMENTS

| | | |
|---|---|---|
| WO | WO96/40267 | 12/1996 |
| WO | WO 96/40923 | 12/1996 |
| WO | WO 99/29728 | 6/1999 |
| WO | WO 99/05396 | 10/1999 |

OTHER PUBLICATIONS

Skelton et al. Biochemistry 1995, vol. 34, pp. 5329-5342.*
Lazar et al. Molecular and Cellular Biology 1988, vol. 8, No. 3, pp. 1247-1252.*
Smilek et al. Proc. Natl. Acad. Sci. USA, 1991, vol. 88, pp. 9633-9637.*
Proudfoot et al. J. Biochem. 1999, vol. 274, No. 45, pp. 32478-32485.*
S.M. Santini and F. Belardelli, Advances in the use of dendritic cells and new adjuvants for the development of therapeutic vaccines, *Stem. Cells* 21 (2003) (4), pp. 495-505.

Y. Manome, P.Y. Wen and A. Hershowitz et al., Monocyte chemoattractant protein-1 (MCP-1) gene transduction: an effective tumor vaccine strategy for non-intracranial tumors, *Cancer Immunol. Immunother.* 41 (1995)(4), pp. 227-235.
D.I. Scott, Immunoblotting, dot-blotting, and ELISPOT assays: methods and applications, *J. Immunoassay* 21 (200)(2-3), pp. 273-296.
J.F. Bach, Cytokine-based immunomodulation of autoimmune diseases: an overview, *Transplant. Proc.* 28 (1996)(6), pp. 3023-3025.
X. Pang, M. Zhang, and A.I. Dayton, Development of dengue virus replicons expressing HIV-1 gp120 and other heterologous genes: a potential future tool for dual vaccination against dengue virus and HIV, *BMC Microbiol.* 1 (2001)(1), p. 28.
B.J. Rollins, JF/MCP-1: an early response gene encodes a monocyte-specific cytokine, *Cancer Cells* 3 (1991)(12), pp. 517-524.
Cox, John C., et al. "Adjuvants—a classificaton and review of their modes of action." Vaccine, 1997, vol. 15, No. 3, pp. 248-256.
Godiska, Ronald, et al. "Human Macrophage-derived Chemokine (MDC), a Novel Chemoattractant for Monocytes, Monocyte-derived Dendritic Cells, and Natural Killer Cells." Journal of Experimental Medicine, May 1997, vol. 185, No. 9, pp. 1595-1604.
Pasquini, S., et al. "Cytokines and costimulatory molecules as genetic adjuvants." Immunology and Cell Biology, 1997, vol. 75, pp. 397-401.
Fulginiti, Vincent A., et al. "Altered Reactivity to Measles Virus." JAMA, Dec. 1967, vol. 202. No. 12, pp. 101-106.
Prince, Gregory A., et al. "Enhancement of Respiratory Syncytial Virus Pulmonary Pathology in Cotton Rats by Prior Intramuscular Inoculation of Formalin-Inactivated Virus." Journal of Virology, Mar. 1986, pp. 721-728.
Girard, Marc. "Prospects for an AIDS Vaccine." Cancer Detection and Prevention, 1990, pp. 411-413.
Barouch, Dan H., et al. "Eventual AIDS vaccine failure in a rhesus monkey by viral escape cytotoxic T lymphocytes." Nature, Jan. 2002, vol. 413, No. 17, pp. 335-339.
Donnelly, John J., et al. "DNA Vaccines." Annu. Rev. Immunal., 1197, vol. 15, pp. 617-618.
Poignard, Pascal, et al. "Neutralizing Antibodies Have Limited Effects on the Control of Established HIV-1 Infection In Vivo." Immunity, 1999, vol. 10, pp. 431-438.
Eng, Vicki M., et al. "The Stimulatory Effects of Interleukin (IL)-12 On Hematopoiesis Are Antagonized by IL-12-induced Interferon y In Vivo." Journal of Experimental Medicine, May 1995, vol. 181, pp. 1893-1989.
Orange, Jordan S., et al. "Mechanism of Interleukin 1Zmediated Toxicities during Experimental Viral Infections: Role of Tumor Necrosis Factor and Glucocorticoids." Journal of Experimental Medicine, Mar. 1995, vol. 181, pp. 901-914.

(Continued)

*Primary Examiner*—Mondesi Robert
*Assistant Examiner*—Bao Qun Li
(74) *Attorney, Agent, or Firm*—Marianne Fuierer; Moore & Van Allen PLLC

(57) ABSTRACT

The present invention relates to compositions and methods of using same to direct an immune response thereby enhancing the efficacy of an antigen containing vaccine by combining a chemokine in conjunction with the vaccine, wherein the choice of the chemokine directs the immune response in either the Th1 or Th2 direction.

10 Claims, 5 Drawing Sheets

OTHER PUBLICATIONS

Wu, George Y., et al. "Receptor-mediated *in Vitro* Gene Transformation by a Soluble DNA Carrier System." The Journal of Biological Chemistry, Apr. 1987, vol. 262, No. 10, pp. 4429-4432.

Frauenschuh, Achim, et al. "Differential polarization of immune responses by co-administration of antigens with chemokines." Vaccine, 2004, vol. 23, pp. 546-554.

Jong J. Kim et al.; In Vivo Engineering of a Cellular Immune Response by Coadministration of IL-12 Expression Vector with a DNA Immunogen; The Journal of Immunology; 1997; pp. 816-826; The American Association of Immunologists.

Lucinda Furci et al.; Antigen-driven C-C Chemokine-mediated HIV-1 Suppression by CD4+ T Cells from Exposed Uninfected Individuals Expressing the Wild-type CCR-5 Allele; J. Exp. Med.; Aug. 4, 1997; pp. 455-459; vol. 186, No. 3; The Rockefeller University Press.

Ranajit Pal et al.; Inhibition of HIV-1 Infection by the B-Chemokine MDC; Science; Oct. 24, 1997; pp. 695-698; vol. 278.

P.H. Naylor and J.W. Hadden, T cell targeted immune enhancement yields effective T cell adjuvants, *Int. Immunopharmacol.* 3 (2003) (8), pp. 1205-1215.

P.H. Naylor and J.W. Hadden, T cell targeted immune enhancement yields effective T cell adjuvants, *Int. Immunopharmacol.* 3 (2003) (8), pp. 1205-1215.

P.H. Naylor and J.W. Hadden, T cell targeted immune enhancement yields effective T cell adjuvants, *Int. Immunopharmacol.* 3 (2003) (8), pp. 1205-1215.

V. Appay and S.L. Rowland-Jones, RANTES: a versatile and controversial chemokine, *Trends Immunol.* 22 (2001) (2), pp. 83-87.

W.J. Karpus and K.J. Kennedy, MIP-1alpha and MCP-1 differentially regulate acute and relapsing autoimmune encephalomyelitis as well as Th1/Th2 lymphocyte differentiation, *J. Leukoc. Biol.* 62 (1997) (5), pp. 681-687.

W.W. Leitner, H. Ying and N.P. Restifo, DNA and RNA-based vaccines: principles, progress and prospects, *Vaccine* 18 (1999) (9-10), pp. 765-777.

K.Q. Xin, Y. Lu and K. Hamajima et al., Immunization of RANTES expression plasmid with a DNA vaccine enhances HIV-1-specific immunity, *Clin. Immunol.* 92 (1999) (1), pp. 90-96.

J.J. Kim, J.S. Yang, T. Dentchev, K. Dang and D.B. Weiner, Chemokine gene adjuvants can modulate immune responses induced by DNA vaccines, *J. Interferon Cytokine Res.* 20 (2000) (5), pp. 487-498.

A. Biragyn, I.M. Belyakov, Y.H. Chow, D.S. Dimitrov, J.A. Berzofsky and L.W. Kwak, DNA vaccines encoding human immunodeficiency virus-1 glycoprotein 120 fusions with proinflammatory chemoattractants induce systemic and mucosal immune responses, *Blood* 100 (2002) (4), pp. 1153-1159.

R. Forster, A.E. Mattis, E. Kremmer, E. Wolf, G. Brem and M. Lipp, A putative chemokine receptor, BLR1, directs B cell migration to defined lymphoid organs and specific anatomic compartments of the spleen, *cell* 87 (1996) (6), pp. 1037-1047.

T.R. Fouts, R. Tuskan and K. Godfrey et al., Expression and characterization of a single-chain polypeptide analogue of the human immunodeficiency virus type 1 gp120-CD4 receptor complex, *J. Virol.* 74 (2000) (24), pp. 11427-11436.

Y. Miyahira, K. Murata and D. Rodriguez et al., Quantification of antigen specific CD8+ T cells using an ELISPOT assay, *J. Immunol. Methods* 181 (1995) (1), pp. 45-54.

K. Yang, S. Wang and K.S. Chang et al., Immune responses and protection obtained with rotavirus VP6 DNA vaccines given by intramuscular injection, *Vaccine* 19 (2001) (23-24), pp. 3285-3291.

J.D. Ahlers, N. Dunlop, D.W. Alling, P.L. Nara and J.A. Berzofsky, Cytokine-in-adjuvant steering of the immune response phenotype to HIV-1 vaccine constructs: granulocyte-macrophage colony-stimulating factor and TNF-alpha synergize with IL-12 to enhance induction of cytotoxic T lymphocytes, *J. Immunol.* 158 (1997) (8), pp. 3947-3958.

D.D. Taub, J.R. Ortaldo, S.M. Turcovski-Corrales, M.L. Key, D.L. Longo and W.J. Murphy, Beta chemokines costimulate lymphocyte cytolysis, proliferation, and lymphokine production, *J. Leukoc. Biol.* 59 (1996) (1), pp. 81-89.

K. Song, Y. Chang and G.J. Prud'homme, Regulation of T-helper-1 versus T-helper-2 activity and enhancement of tumor immunity by combined DNA-based vaccination and nonviral cytokine gene transfer, *Gene Ther.* 7 (2000) (6), pp. 481-492.

P.R. Hutchings, G. Cambridge, J.P. Tite, T. Meager and A. Cooke, The detection and enumeration of cytokine-secreting cells in mice and man and the clinical application of these assays, *J. Immunol. Methods* 120 (1989) (1), pp. 1-8.

D.M. Pardoll, Paracrine cytokine adjuvants in cancer immunotherapy, *Annu. Rev. Immunol.* 13 (1995), pp. 399-415.

S. Gurunathan, D.M. Klinman and R.A. Seder, DNA vaccines: immunology, application, and optimization, *Annu. Rev. Immunol.* 18 (2000), pp. 927-974.

B. Moser and P. Loetscher, Lymphocyte traffic control by chemokines, *Nat. Immunol.* 2 (2001) (2), pp. 123-128.

D. Behringer, V. Kresin, R. Henschler, R. Mertelsmann and A. Lindemann, Cytokine and chemokine production by CD34+ haemopoietic progenitor cells: detection in single cells, *Br. J. Haematol.* 97 (1997) (1), pp. 9-14.

G. Deliyannis, J.S. Boyle, J.L. Brady, L.E. Brown and A.M. Lew, A fusion DNA vaccine that targets antigen-presenting cells increases protection from viral challenge, *Proc. Natl. Acad. Sci. U.S.A.* 97 (2000) (12), pp. 6676-6680.

M. Corr, A. von Damm, D.J. Lee and H. Tighe, In vivo priming by DNA injection occurs predominantly by antigen transfer, *J. Immunol.* 163 (1999) (9), pp. 4721-4727.

* cited by examiner

SEQUENCE LISTING

<160> NUMBER OF SEQ ID NOS: 4

<210> SEQ ID NO 1
<211> LENGTH: 2923
<212> TYPE: DNA
<213> ORGANISM: Homo sapiens

<400> SEQUENCE: 1

```
gagacataca ggacagagca tggctcgcct acagactgca ctcctggttg tcctcgtcct      60
ccttgctgtg gcgcttcaag caactgaggc aggccoctac ggcgccaaca tggaagacag     120
cgtctgctgc cgtgattacg tccgttaccg tctgcccctg cgcgtggtga aacacttcta     180 ctggaccctca gactcctgcc cgaggcctgg cgtggtgttg ctaaccttca gggataagga     240
gatctgtgcc gatcccagag tgccctgggt gaagatgatt ctcaataagc tgagccaatg     300
aagagcctac tctgatgacc gtggccttgg ctcctccagg aaggctcagg agccctacct     360
ccctgccatt atagctgctc cccgccagaa gcctgtgcca actctctgca ttccctgatc     420
tccatccctg tggctgtcac ccttggtcac ctccgtgctg tcactgccat ctcccccctg     480 accctctaa cccatcctct gcctccctcc ctgcagtcag agggtcctgt tcccatcagc     540
gattcccctg cttaaaccct tccatgactc cccactgccc taagctgagg tcagtctccc     600
aagcctggca tgtggccctc tggatctggg ttccatctct gtctccagcc tgcccacttc     660
ccttcatgaa tgttgggttc tagctccctg ttctccaaac ccatactaca catcccactt     720
ctgggtcttt gcctgggatg ttgctgacac tcagaaagtc ccaccacctg cacatgtgta     780
gccccaccag ccctccaagg cattgctcgc ccaagcagct ggtaattcca tttcatgtat     840
tagatgtccc ctggccctct gtccctctt aatacccta gtcacagtct ccgcagattc     900
ttgggatttg ggggttttct ccccaccctc tccactagtt ggaccaaggt ttctagctaa     960
gttactctag tctccaagcc tctagcatag agcactgcag acaggccctg gctcagaatc    1020
agagcccaga aagtggctgc agacaaaatc aataaaacta atgtccctcc cctctccctg    1080
ccaaaaggca gttacatatc aatacagaga ctcaaggtca ctagaaatgg gccagctggg    1140
```

-continued

| | |
|---|---|
| tcaatgtgaa gccccaaatt tgcccagatt caccttcctt cccccactcc cttttttttt | 1200 |
| tttttttttt tgagatggag tttcgctctt gtcacccacg ctggagtgca atggtgtggt | 1260 |
| cttggcttat tgaagcctct gcctcctggg ttcaagtgat tctcttgcct cagcctcctg | 1320 |
| agtagctggg attacaggtt cctgctacca cgcccagcta attttttgtat ttttagtaga | 1380 |
| gacgaggctt caccatgttg gccaggctgg tctcgaactc ctgtcctcag gtaatccgcc | 1440 |
| cacctcagcc tcccaaagtg ctgggattac aggcgtgagc cacagtgcct ggcctcttcc | 1500 |
| ctctccccac tgccccccc aacttttttt tttttttttat ggcagggtct cactctgtcg | 1560 |
| cccaggctgg agtgcagtgg cgtgatctcg gctcactaca acctcgacct cctgggttca | 1620 |
| agtgattctc ccaccccagc ctcccaagta gctgggatta caggtgtgtg ccactacggc | 1680 |
| tggctaattt ttgtattttt agtagagaca ggtttcacca tattggccag ctggtcttg | 1740 |
| aactcctgac ctcaagtgat ccaccttcct tgtgctccca aagtgctgag attacaggcg | 1800 |
| tgagctatca cacccagcct ccccttttt ttcctaatag gagactcctg tacctttctt | 1860 |
| cgttttacct atgtgtcgtg tctgcttaca tttccttctc ccctcaggct ttttttgggt | 1920 |
| ggtcctccaa cctccaatac ccaggcctgg cctcttcaga gtaccccca ttccactttc | 1980 |
| cctgcctcct tccttaaata gctgacaatc aaattcatgc tatggtgtga aagactacct | 2040 |
| ttgacttggt attataagct ggagttatat atgtatttga aaacagagta aatacttaag | 2100 |
| aggccaaata gatgaatgga agaattttag gaactgtgag aggggacaa ggtgaagctt | 2160 |
| tcctggccct gggaggaagc tggctgtggt agcgtagcgc tctctctctc tgtctgtggc | 2220 |
| aggagccaaa gagtagggtg taattgagtg aaggaatcct gggtagagac cattctcagg | 2280 |
| tggttgggcc aggctaaaga ctgggagttg ggtctatcta tgccttttctg gctgattttt | 2340 |
| gtagagacgg ggttttgcca tgttacccag gctggtctca aactcctggg ctcaagcgat | 2400 |
| cctcctggct cagcctccca aagtgctggg attacaggcg tgaatcactg cgcctggctt | 2460 |
| cctcttcctc ttgagaaata ttcttttcat acagcaagta gggacagca gtgtcccagg | 2520 |
| taaaggacat aaatgttaca agtgtctggt cctttctgag ggaggctggt gccgctctgc | 2580 |
| agggtatttg aacctgtgga attggaggag gccatttcac tccctgaacc cagcctgaca | 2640 |
| aatcacagtg agaatgttca ccttataggc ttgctgtggg gctcaggttg aaagtgtggg | 2700 |
| gagtgacact gcctaggcat ccagctcagt gtcatccagg gcctgtgtcc ctcccgaacc | 2760 |
| cagggtcaac ctgcctgcca caggcactag aaggacgaat ctgcctactg cccatgaacg | 2820 |
| gggccctcaa gcgtcctggg atctccttct ccctcctgtc ctgtccttgc ccctcaggac | 2880 |
| tgctggaaaa taaatccttt aaaatagtaa aaaaaaaaa aaa | 2923 |

<210> SEQ ID NO 2
<211> LENGTH: 725
<212> TYPE: DNA
<213> ORGANISM: Homo sapiens

<400> SEQUENCE: 2

| | |
|---|---|
| ctaacccaga aacatccaat tctcaaactg aagctcgcac tctcgcctcc agcatgaaag | 60 |
| tctctgccgc ccttctgtgc ctgctgctca tagcagccac cttcattccc caagggctcg | 120 |
| ctcagccaga tgcaatcaat gccccagtca cctgctgtta aacttcacc aataggaaga | 180 |
| tctcagtgca gaggctcgcg agctatagaa gaatcaccag cagcaagtgt cccaaagaag | 240 |
| ctgtgatctt caagaccatt gtggccaagg agatctgtgc tgaccccaag cagaagtggg | 300 |

```
ttcaggattc catggaccac ctggacaagc aaacccaaac tccgaagact tgaacactca    360
ctccacaacc caagaatctg cagctaactt attttcccct agctttcccc agacaccctg    420
ttttatttta ttataatgaa ttttgtttgt tgatgtgaaa cattatgcct taagtaatgt    480
taattcttat ttaagttatt gatgttttaa gtttatcttt catggtacta gtgttttta    540 gatacagaga cttggggaaa ttgcttttcc tcttgaacca cagttctacc cctgggatgt    600
tttgagggtc tttgcaagaa tcattaatac aaagaatttt ttttaacatt ccaatgcatt    660
gctaaaatat tattgtggaa atgaatattt tgtaactatt acaccaaata aatatatttt    720
tgtac                                                                725
```

<210> SEQ ID NO 3
<211> LENGTH: 276
<212> TYPE: DNA
<213> ORGANISM: Homo sapiens

<400> SEQUENCE: 3

```
atgaaggtct ccgcggcacg cctcgctgtc atcctcattg ttactgccct ctgcgctcct     60
gcatctgcct ccccatattc ctcggacacc acaccctgct gctttgccta cattgcccgc    120
ccactgcccc gtgcccacat caaggagtat ttctacacca gtggcaagtg ctccaaccca    180
gcagtcgtct tgtcacccg aaagaaccgc caagtgtgtg ccaacccaga gaagaaatgg    240
gttcgggagt acatcaactc tttggagatg agctag                             276
```

<210> SEQ ID NO 4
<211> LENGTH: 663
<212> TYPE: DNA
<213> ORGANISM: Homo sapiens
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t

<400> SEQUENCE: 4

```
cagagctcaa gtctgaactc tacctccaga cagaatgaag ttcatctcga catctctgct     60
tctcatgctg ctggtcagca gcctctctcc agtccaaggt gttctggagg tctattacac    120
aagcttgagg tgtagatgtg tccaagagag ctcagtcttt atccctagac gcttcattga    180
```

-continued

```
tcgaattcaa atcttgcccc gtgggaatgg ttgtccaaga aaagaaatca tagtctggaa    240
gaagaacaag tcaattgtgt gtgtggaccc tcaagctgaa tggatacaaa gaatgatgga    300
agtattgaga aaaagaagtt cttcaactct accagttcca gtgtttaaga gaaagattcc    360
ctgatgctga tatttccact aagaacacct gcattcttcc cttatccctg ctctgggatt    420
ttagttttgt gcttagttaa atcttttcca gggagaaaga acttccccat acaaataagg    480
catgaggact atgtaaaaat aaccttgcag gagctggatg gggggccaaa ctcaagcttc    540
tttcactcca caggcaccct attntacact tgggggtttt gcnttctttn tttcntcagg    600
ggggggaaa gtttcttttg gaaantagtt nttccagttn ttaggtatta cagggttntt     660
ttt                                                                  663
```

US 7,708,983 B2

DIRECTIONAL INDUCTION OF IMMUNE RESPONSE BY CO-ADMINISTRATION OF ANTIGENS WITH CHEMOKINES

CROSS-REFERENCE TO RELATED APPLICATIONS

This application claims priority to U.S. Provisional Application No. 60/700,690 filed on Jul. 19, 2005 and U.S. patent application Ser. No. 11/072,798 which is a continuation of application Ser. No. 10/445,790, filed on May 27, 2003, now U.S. Pat. No. 6,919,319 and a divisional of application Ser. No. 09/591,992 filed on Jun. 12, 2000, now U.S. Pat. No. 6,569,418, which claims priority to International Patent Application No. PCT/US98/26291, filed Dec. 11, 1998, which in turn is based on and claims priority to U.S. Patent Application No. 60/069,281 filed Dec. 11, 1997, the contents of which are hereby incorporated by reference herein for all purposes.

BACKGROUND OF THE INVENTION

1. Field of the Invention

The present invention relates to compositions and methods of using same to direct an immune response thereby enhancing the efficacy of an antigen containing vaccine by combining a chemokine in conjunction with the vaccine, wherein the choice of the chemokine directs the immune response in either the Th1 or Th2 direction.

2. Background of the Related Art

Immunization procedures often are made more effective by delivering immnunogens along with empirical preparations defined as adjuvants. These preparations have the effect of enhancing immune response by improving antigen presentation, essentially by inducing local innate immune responses, that in-turn increase expression of co-stimulatory molecules and cytokines that stimulate T cells growth and differentiation and recall antigen-presenting cells at the site of immunization. In recent times several investigators have tried to enhance antigen presentation by introducing immuno-stimulatory cytokines along with the immunogen [1], [2] and [3]. A similar approach has been attempted to manipulate T helper response towards cellular (Th1) or humoral (Th2) immunity [3]. These studies reflect the intent to rationally induce and modulate immune response in a targeted, rather than in an empirical manner. Chemoattractant cytokines, or chemokines (CC), function as immunologic mediators by attracting specific subsets of leukocytes to either sites of inflammation (inflammatory cytokines) or, when involved in homing processes, to lymphoid organs, (constitutively expressed cytokines) [4]. Therefore, chemokines are relevant to the pathogenesis of many diseases such as chronic infections, inflammatory and autoimmune diseases, transplant rejection, and cancer [5], [6] and [7]. Further, chemokines and their receptors are also involved in the selective induction of both Th1 and Th2 responses [4].

In early studies, RANTES was found to enhance immunity to HIV in DNA vaccines [8] and [9] whereas MCP-1 DNA appeared to be an effective means of boosting immune responses against experimental tumors [10]. In addition, chemokines and antigens have been linked to create new, more potent immunogens [11] and [12]. However, studies comparing the effects of different chemokines on immune response profiles to a specific antigen have not been conducted. DNA immunization is presently being developed as an inexpensive and safe means for providing immunizations to large numbers of people. One of the shortcomings of this approach is the relatively weak immune response triggered by DNA vaccines. The present invention provides for the administration of select chemokines to enhance the immune response to DNA vaccines.

Because of their ability to attract discrete sub-populations of leukocytes to sites of inflammation and antigen presentation, chemokines are key agents in eliciting immune responses. In addition, chemokines reportedly can influence the T helper response towards a Th1 (i.e. cell mediated) or Th2 (i.e. humoral) profile, according to the differential distribution of receptors on target cells.

Therefore, the use of chemokines in immunization may contribute a tailored adjuvant-like effect. In addition, since some diseases are known to significantly alter the Th profile of the immune response, vaccination programs in areas endemic for such diseases can be hampered by the prevalence of a skewed immune response. The use of chemokines in adjuvant preparation has the potential to rebalance the immune response, thus, improving the success rate of a vaccination program in this context.

SUMMARY OF THE INVENTION

The present invention relates generally to the use of chemokines, particularly chemokines that attract lymphocytes or antigen presenting cells, for enhancing an immune response to an antigen, particularly to a vaccine antigen.

Preferred chemokines according to the practice of the present invention include RANTES (regulated on activation, normal T cell expressed and secreted), a chemokine, which has receptors on both Th1 and Th2, cells, MCP-1 (monocyte chemoattractant protein), which is Th1-type associated, and the Th2-type associated chemokine BLC (B lymphocyte chemoattractant) and MDC (macrophage-derived chemoattractant). The present inventors have studied the immunomodulating properties of these chemokines in conjunction with DNA immunization, using HIV-$1_{BaL}$ gp120 and membrane-bound HIV-$1_{BaL}$ gp160 as antigens and have discovered that chemokines modulate immune responses according to their Th-type polarization. Further, the chemokines can be ranked in the following order of induction of Th-2 vs Th-1 responses: BLC (inducing mostly humoral responses), MDC, MCP-1 and RANTES (inducing mostly cellular responses).

In one aspect, the present invention provides for developing and optimizing vaccination regimens, for directing and/or combining Th-type responses.

In one aspect, the invention relates to a method for enhancing the efficacy of a vaccine and directing a tailored adjuvant-like effect in a subject. The method generally comprises administering to the subject: a first component selected from the group consisting of: (i) an antigen against which an immune response is desired in the subject; and (ii) a nucleic acid encoding the antigen of (i). In addition to the first component, the subject is also administered a second component selected from the group consisting of: (i) a chemokine selected from the group consisting of RANTES, MCP-1, and BLC, or a functional equivalent (as defined herein) of said chemokine; and (ii) a nucleic acid encoding the chemokine of (i). The first component and second component are administered in an immunizingly effective amount.

In another aspect of the invention, the second component is administered concurrently with the first component. The second component may also be administered within a time period before or after administration of the first component, which time period is sufficient to achieve the desired immunoresponse and the efficacy of the vaccine.

The first component may be any of a wide variety of antigens known in the art. However, in a preferred embodiment of the invention, the first component is an HIV antigen, including HIV-1 and HIV-2. Preferred HIV antigens include gp120, gp 41, gp 160 antigen, including analogs, derivatives and fragments thereof which produce an immune response (i.e., polypeptides which are functionally equivalent in that they produce an antibody response wherein the antibodies produced by such response will bind to native gp120), which antibodies also have specificity for a native HIV gp120.

In another aspect, the invention relates to a nucleic acid encoding both the first component and the second component.

In a method aspect of the invention, the first component and the second component are provided as nucleotides on the same or on separate sequences and are administered directly to the subject. The nucleotide sequence(s) may be used to transform a cell. The nucleotide sequence may be directly administered to a subject or the transformed cell is administered to the subject. The first component suitably comprises a nucleic acid encoding a HIV antigen, preferably a gp120 antigen. The subject is preferably a human and may be HIV positive or may exhibit behavioral patterns or occupational factors associated with risk of becoming HIV positive.

In another aspect, the invention relates to a method for improving the speed of an antibody response to a soluble antigen in a subject, comprising co-administering to the subject the soluble antigen with BLC. The soluble antigen is preferably an HIV antigen, more preferably a gp120 antigen. The subject is preferably a human.

In yet another aspect, the invention provides a method for modulating (inducing or enhancing) a cellular or a humoral response in a subject in need thereof, the method comprising administering to the subject an effective amount of RANTES, BLC or MCP-1.

In a still further aspect, the present invention relates to compositions for achieving the various method aspects of the invention. For example, in one aspect, the invention relates to a composition comprising a first component selected from the group consisting of: (i) an antigen against which an immune response is desired in the subject, and (ii) a nucleic acid encoding the antigen of (i); along with a second component selected from the group consisting of: (i) a chemokine selected from the group consisting of RANTES, MCP-1 and BLC, or a functional equivalent of said chemokine, and (ii) a nucleic acid encoding the chemokine of (i). This composition preferably also comprises one or more of each of the following pharmaceutically acceptable components including carriers; excipients; auxiliary substances; adjuvants; wetting agents; emulsifying agents; pH buffering agents; and other components known for use in vaccine or other pharmaceutical compositions.

The invention also relates to a nucleic acid comprising: a first nucleic acid sequence encoding an antigen against which an immune response is desired in the subject; and a second nucleic acid sequence encoding a chemokine selected from the group consisting of RANTES, MCP-1, and BLC, or a functional equivalent of said chemokine. The first and second nucleic acid sequences are preferably expressed in a coordinated manner upon introduction into a subject to produce an amount of the first component that is immunogenic and an amount of the second component that is effective to enhance the efficacy of the vaccine. A related aspect of the invention involves the administration of this nucleic acid to a subject in need thereof to elicit an immune response to the antigen. The nucleic acid is suitably administered as a component of a pharmaceutical composition and may be administered directly to the subject and/or introduced into a suitable host cell and said suitable host cell is administered to the subject. The host cell may be obtained from the subject or from a cell culture originating from one or more cells obtained from the subject.

In another aspect, the present invention relates use of the compositions comprising an antigen and chemokine in a pharmaceutical for treating HIV, wherein the chemokine selectively recruits specific cell subsets to bias the immune responses toward Th1- or Th2-type patterns.

DETAILED DESCRIPTION OF THE INVENTION

Definitions

Figure 1:
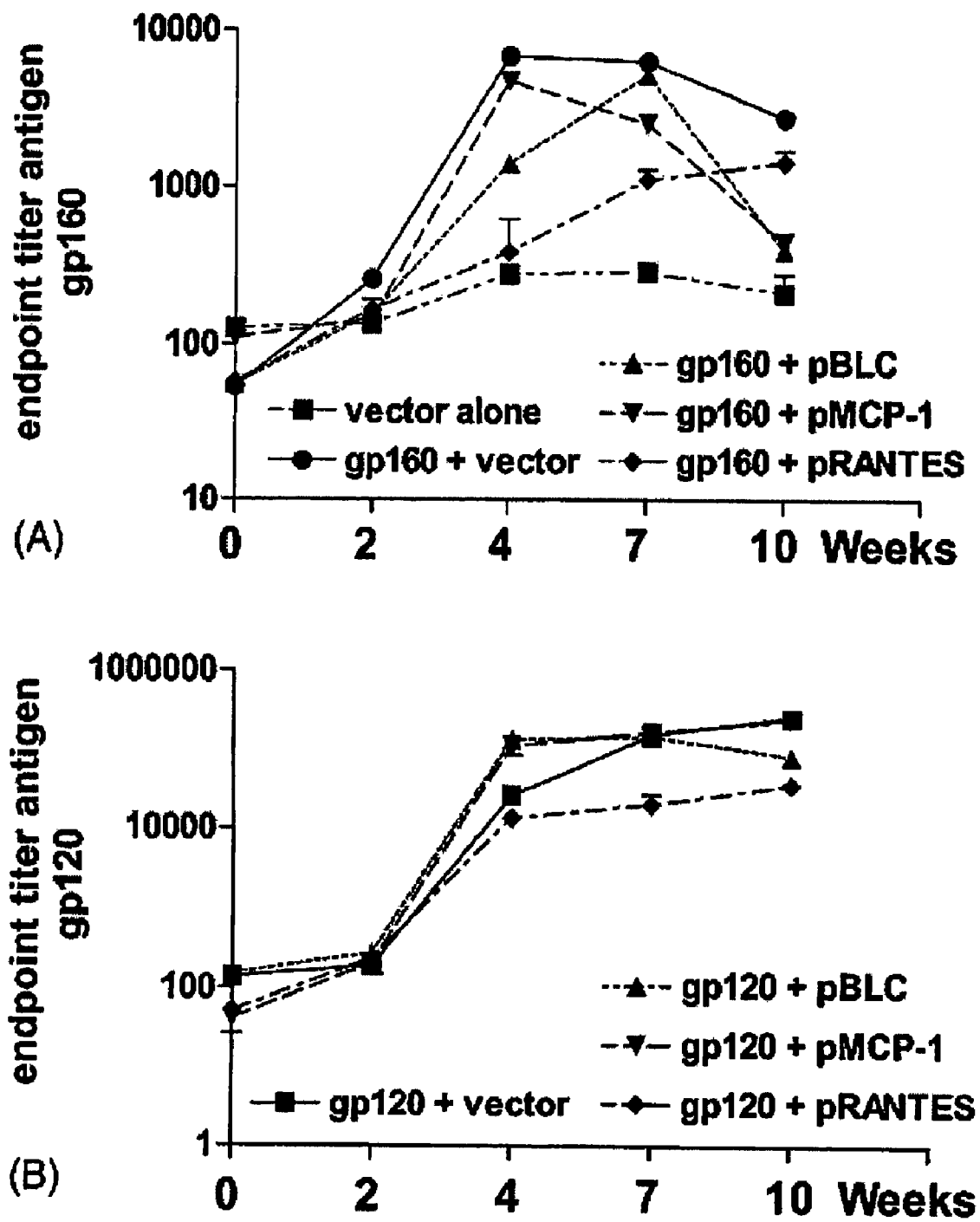
FIG. 1 shows the total anti-IgG Ab titer after DNA vaccination with the antigens HIV-1$_{BaL}$gp160 (Panel A) or HIV-1$_{BaL}$gp120 (Panel B), respectively, and different plasmid-derived chemokines: 11 days after an injection of cardiotoxin (50 μl of 10 μM) three DNA co-injections (to 100 μg of DNA per leg) of plasmids encoding for one of the antigens and one of the chemokines BLC, MCP-1 or RANTES or the control vector, respectively, were performed i.m. into each quadricep at Weeks 0, 2 and 4. Blood samples were drawn prior to each injection and at Weeks 7 and 10. Antibody titers were determined on heat inactivated sera. The titer was obtained by capture ELISA (coating the plate with anti-gp120 and capturing with rgp140). Groups were of 6 animals each. BLC: B lymphocyte chemoattractant; MCP-1: monocyte chemoattractant protein-1; RANTES: regulated on activation, normal T cell expressed and secreted.

The term "functional equivalent" with respect to a polypeptide (e.g., a chemokine or antigen) as used herein refers to a polypeptide sequence comprising the full length amino acid sequence of the polypeptide, or comprising a fragment, analogue, derivative or truncation isoform of the polypeptide. Functional equivalents also include, for example, the polypeptide, or its fragment, analogue, derivative or truncation isoform, in salt, complex, or analog form. Functional equivalents retain some or all of the biological activity of the corresponding polypeptide. Where the polypeptide referred to is an antigen, "biological activity" refers to the ability of the functional equivalent to bind to an antibody that will also bind to the native antigen.

The present invention provides for compositions and methods for modifying or tailoring an immune response of a desired profile, regarded as most adequate to fight a pathogen or a neoplastic cell, or to "redirect" immune response in a particular immunologic background, such as in a Th1 or Th2 skewed immunity.

The methods comprise administering to a subject an immunogenic amount of one or more purified antigens against which an immune response is desired in the subject in conjunction with an amount of one or more purified chemokines, or fragments, derivatives, analogues and/or truncation isoforms thereof, effective to enhance the immune response against the antigen.

While any chemokine may be employed according to the present invention, the chemokine is preferably selected from the following table 1:

| Chemokine Class | Chemokines | Abbreviations | Accession Number |
| --- | --- | --- | --- |
| CC Chemokines | Macrophage-derived chemokine | MDC/STCP-1 | u83171; u83239 |
| | Monocyte chemotactic protein 1 | MCP-1 | x14768 |
| | Monocyte chemotactic protein 2 | MCP-2 | X99886 |
| | Monocyte chemotactic protein 3 | MCP-3 | x72308; s57464 |
| | Monocyte chemotactic protein 4 | MCP-4 | u46767 |
| | activated macrophage specific chemokine 1 | AMAC-1 | Y13710 |
| | Macrophage inflammatory protein 1 alpha | MIP-1α | AF043339; X03754; D90144 |
| | Macrophage inflammatory protein 1 beta | MIP-1β | j04130; d90145 |
| | Macrophage inflammatory protein 1 gamma | MIP-1γ | |
| | Macrophage inflammatory protein 1 delta | MIP-1δ | AF031587 |
| | Macrophage inflammatory protein 2 alpha | MIP-2α | AF043340 |
| | Macrophage inflammatory protein 3 alpha | MIP-3α | u77035 |
| | Macrophage inflammatory protein 3 beta | MIP-3β | u77180 |
| | Regulated upon activation, normal T cell expressed and secreted (and its variants) | RANTES | M21211 |
| | I-309 | | M57502 |
| | EBI1-ligand chemokine | ELC | AB000887 |
| | Pulmonary and activation regulated chemokine | PARC/DC-CK-1/MIP4 | AB000221 |
| | Liver and activation-regulated chemokine | LARC | D86955 |
| | Thymus and activation regulated chemokine | TARC | D43767 |
| | Eotaxin (and variants) | | D49372; Z69291; Z75669; Z75668 |

-continued

| Chemokine Class | Chemokines | Abbreviations | Accession Number |
|---|---|---|---|
| | Human chemokine 1 | HCC1; NCC2 | Z49270; z49269 |
| | Human chemokine 2 | HCC2; NCC3, MIP-5, MIP-1δ | Z70292 |
| | Human chemokine 3 | HCC3 | Z70293 |
| | IL-10-inducible chemokine | HCC4 | U91746 |
| | liver-expressed chemokine. | LEC; HCC4; NCC4 | AB007454 |
| | 6Ckine | | AF001979 |
| | Exodus 1 | | u64197 |
| | Exodus 2 | | U88320 |
| | Exodus 3 | | U88321 |
| | thymus-expressed chemokine | TECK | U86358 |
| | Secondary Lymphoid tissue chemokine | SLC | AB002409 |
| | Lymphocyte and Monocyte chemoattractant; Monotactin | LMC | AF055467 |
| | Activation-induced, chemokine-related molecule | ATAC | x86474 |
| | Myeloid progenitor inhibitory factor-1 | MPIF-1; MIP-3 or ckbeta8 | u85767 |
| | Myeloid progenitor inhibitory factor-2 | MPIF-2 | u85768 |
| | Stromal cell-derived factor 1 alpha | SDF-1α; PBSF | L36034 |
| CXC chemokines | Stromal cell-derived factor 1 beta | SDF-1β; PBSF | L36033 |
| | B-cell-attracting chemokine 1 | BLC | AJ002211 |
| | HuMIG | | x72755 s60728 |
| | H174 | | AF002985 |
| | Interferon-stimulated T-cell alpha chemoattractant | I-TAC | AF030514 |
| | Interleukin-8 | IL-8 | m17017; y00787 |
| | IP-10 | | X02530 |
| | platelet factor 4 | PF4 | M20901 |
| | growth-regulated gene-alpha | GRO-α | J03561 |
| | growth-regulated gene-beta | GRO-β | M36820 |
| | growth-regulated gene-gamma | GRO-γ | M36821 |
| | Neutrophil-activating protein 2 | NAP-2; CTAP-3 | M54995; M38441 |
| | ENA-78 | | L37036 |
| | granulocyte chemotactic protein 2 | GCP-2 | Y08770 |
| C-CHEMOKINES | LYMPHOTACTIN | SCM-1 | D63789 D63790 |
| CX₃C-CHEMOKINES | Fractalkine/neurotactin | | U91835 U84487 |

In one aspect, the purified chemokine(s), or fragment(s), derivative(s), analogue(s) and/or truncation isoforms thereof, are administered to the subject concurrently with (e.g. in the same composition with) the purified antigen or antigens against which an immune response is desired. In another, aspect, the purified chemokine(s), or fragment(s), derivative(s), analogue(s) and/or truncation isoforms thereof, are administered either before or after the administration of one or more purified antigens against which immunity is desired in the subject, but is administered within such time that the chemokine(s) enhance the immune response to the one or more antigens.

In yet another specific embodiment, the chemokine is a purified derivative of the protein, which derivative has one or more insertions of or substitutions with one or more non-classical amino acids relative to a corresponding wildtype chemokine, which derivative will enhance the efficacy of the vaccine. In yet another specific embodiment, the chemokine is a purified derivative of the protein that has only one or more conservative substitutions in sequence relative a corresponding wildtype chemokine, which derivative will enhance the efficacy of the vaccine. The chemokines useful in the present invention may be derived from any suitable source and obtained by any method known in the art.

Preferably, the chemokine(s) are of the same species as the subject to which the vaccine is administered. In a preferred embodiment, one or more human chemokines are administered to a human subject.

The present invention also provides compositions to enhance the efficacy of an antigen containing vaccine in a subject, which compositions comprise a purified first nucleic acid comprising a nucleotide sequence encoding one or more antigen(s) and a purified second nucleic acid comprising a nucleotide sequence encoding one or more chemokines, or fragments or derivatives, including truncation isoforms, thereof, wherein the nucleotide sequences encoding the antigens and the chemokine(s) are operably linked to one or more gene regulatory elements such that, upon introduction of said first and second nucleic acids into a suitable cell (e.g., a cell of the subject), the antigen(s) and chemokine(s) are expressed in a coordinated manner and the antigen(s) are expressed in an immunogenic amount and the chemokine(s) are expressed in an amount effective to enhance the immune response against the antigen, relative to a corresponding immune response in the absence of such chemokine(s).

Any nucleic acid comprising a nucleotide sequence encoding one or more chemokine proteins, or fragments or derivatives, thereof (including truncation isoforms), that are capable of directing an immune response to the antigen can be used in the methods and compositions of the present invention. Such compositions containing a nucleotide sequence encoding an antigen are often referred to as DNA vaccines.

Such DNA vaccines are produced by any method known in the art for constructing an expression plasmid/vector containing the nucleotide sequences of the antigen(s) and/or chemokine(s) to be expressed, wherein the plasmid/vector is suitable for expression of the encoded proteins in the subject or in cells recombinant for the expression vector. Such expression vectors may contain various promoters, terminators and polyadenylation coding regions to control the expression of the encoded protein.

The DNA vaccine can be administered by any method known in the art for administration of DNA. The DNA vaccine may be delivered either directly, in which case the subject is directly exposed to the DNA vaccine such that the DNA enters and is expressed in cells of the subject, or indirectly, in which case, the DNA vaccine is first introduced into suitable cells by any method known in the art in vitro, then the cells containing the DNA vaccine are transplanted into the subject.

In a specific embodiment, the DNA vaccine is directly administered in vivo, where it is expressed to produce the encoded antigens and chemokine(s). This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, $J.$ $Biol.$ $Chem.$ 262:4429-4432 (1987)) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In a preferred embodiment, the nucleic acid of a DNA vaccine is injected into the muscle of the subject to be immunized.

Another approach is to introduce the nucleic acid of the DNA vaccine into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign nucleic acid into cells and may be used in accordance with the present invention. Usually, the method of transfer includes the transfer of a selectable marker to the cells. The cells are then placed under selection to isolate those cells that have taken up and are expressing the transferred gene.

Cells into which a DNA vaccine can be introduced for purposes of immunization encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

The resulting recombinant cells can be delivered to a subject by various methods known in the art. In a preferred embodiment, the recombinant cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The cells can also be encapsulated in a suitable vehicle and then implanted in the subject The amount of cells envisioned for use depends on the desired effect, subject state, etc., and can be determined by one skilled in the art.

By way of example, an expression vector is constructed with the promoter, enhancer and intron A of human cytomegalovirus (CMV) and the termination and polyadenylation sequences of bovine growth hormone in a plasmid backbone. Additionally, the nucleotide sequence for signal sequence of tissue plasminogen activator is either substituted for the signal sequence of the antigen, if the antigen has a signal sequence or is added onto the amino-terminus of the antigen, thereby eliminating the dependence on viral proteins for expression (e.g. in the case of gp120 expression, rev and env proteins are required unless the HIV-1 signal sequence is so substituted). The resulting formulation is then injected intramuscularly.

For the practice of the present invention, the nucleotide sequence for the one or more chemokines, or fragments, derivatives, or analogues thereof, can either be incorporated into the same expression vector containing the nucleotide sequence encoding the antigen in such a manner that the chemokine(s) are expressed. Alternatively, the nucleotide sequence encoding the chemokine(s), or fragment(s), derivative(s) or analogue(s) thereof, can be cloned into a separate expression vector (e.g., as described above for the expression vector containing the sequences coding for antigen) and the expression vector that expresses the antigen(s) mixed with the expression vector that expresses the chemokine(s). The mixture of the two expression vectors can then be administered to the subject.

The methods and compositions of the present invention may be used as a vaccine in a subject in which immunity for the antigen(s) is desired. Such antigens can be any antigen known in the art to be useful in a vaccine formulation. The methods and compositions of the present invention can be used to enhance the efficacy of any vaccine known in the art and equally important can direct an immune response in either the Th1 or Th2 direction. The vaccine of the present invention may be used to modulate, enhance and/or direct an immune response to infectious agents and diseased or abnormal cells, such as but not limited to bacteria, parasites, fungi, viruses, tumors and cancers. The compositions of the invention may be used to either treat or prevent a disease or disorder amenable to treatment or prevention by generating an immune response to the antigen provided in the composition.

In one preferred embodiment, the antigen(s) are proteins, fragments or derivatives, including truncation isoforms, thereof, encoded by any genes of the HIV genome including the env, gag, pol, nef, vif, rev, and tat genes. In a more preferred embodiment, the antigen is an HIV-associated gp120 protein.

The methods and compositions of the present invention may be used to elicit a humoral and/or a cell-mediated response against the antigen(s) of the vaccine in a subject. In one specific embodiment, the methods and compositions elicit a humoral response against the administered antigen in a subject. In another specific embodiment, the methods and compositions elicit a cell-mediated response against the administered antigen in a subject. In a preferred embodiment, the methods and compositions elicit both a humoral and a cell-mediated response.

The subjects to which the present invention is applicable may be any mammalian or vertebrate species, which include, but are not limited to cows, horses, sheep, pigs, fowl (e.g., chickens), goats, cats, dogs, hamsters, mice and rats, monkeys, rabbits, chimpanzees, and humans. In a preferred embodiment, the subject is a human. The compositions and methods of the invention can be used to either prevent a disease or disorder, or to treat a particular disease or disorder, where an immune response against a particular antigen or antigens is effective to treat or prevent the disease or disorder. Such diseases and disorders include, but are not limited to, viral infections, such as HIV, CMV, hepatitis, herpes virus, measles, etc, bacterial infections, fungal and parasitic infections, cancers, and any other disease or disorder amenable to treatment or prevention by eliciting an immune response against a particular antigen or antigens. In another preferred embodiment, the subject is infected or at risk of being infected with HIV virus.

In another preferred embodiment the invention provides methods and compositions to enhance the efficacy of an HIV vaccine and direct an immune response wherein such a vaccine can be administered to either prevent or treat HIV.

Chemokine proteins and nucleic acids can be obtained by any method known in the art. Chemokine nucleotide and amino acid sequences are available in public databases such as Genbank and are also published in various references known to those of skill in the art.

Chemokines used herein include, but are not limited to, chemokines from mice, hamsters, dogs, cats, monkeys, rabbits, chimpanzees, and human. In one preferred embodiment, the chemokine is of human origin.

Any vertebrate cell potentially can serve as the nucleic acid source for the isolation of chemokine nucleic acids. The nucleic acid sequences encoding the chemokine(s) can be isolated from vertebrate, mammalian, human, porcine, bovine, feline, avian, equine, canine, as well as additional primate sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from cDNA, cDNA is generated from totally cellular RNA or mRNA by methods that are well known in the art. The gene may also be obtained from genomic DNA, where DNA fragments are generated (e.g. using restriction enzymes or by mechanical shearing), some of which will encode the desired gene. The linear DNA fragments can then be separated according to size by standard techniques, including but not limited to, agarose and polyacrylamide gel electrophoresis and column chromatography. Once the DNA fragments are generated, identification of the specific DNA fragment containing all or a portion of the chemokine gene may be accomplished in a number of ways. A preferred method for isolating a chemokine gene is by the polymerase chain reaction (PCR), which can be used to amplify the desired chemokine sequence in a genomic or cDNA library or from genomic DNA or cDNA that has not been incorporated into a library. Oligonucleotide primers which would hybridize to chemokine sequences can be used as primers in PCR.

Additionally, a portion of the chemokine (of any species) gene or its specific RNA, or a fragment thereof, can be purified (or an oligonucleotide synthesized) and labeled, the generated DNA fragments may be screened by nucleic acid hybridization to the labeled probe. Those DNA fragments with substantial homology to the probe will hybridize.

Chemokine nucleic acids can be also identified and isolated by expression cloning using, for example, anti-chemokine antibodies for selection.

Chemokine proteins and derivatives, analogs and fragments of chemokine proteins can be obtained by any method known in the art, including but not limited to recombinant expression methods, purification from natural sources, and chemical synthesis.

For example, chemokines can be obtained by recombinant protein expression techniques. For recombinant expression, the chemokine gene or portion thereof is inserted into an appropriate cloning vector for expression in a particular host cell. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and chemokine gene may be modified by homopolymeric tailing. Recombinant molecules can be introduced into host cells via transformation, transfection, infection, electroporation, etc., so that many copies of the gene sequence are generated.

In specific embodiments, transformation of host cells with recombinant DNA molecules that incorporate the isolated chemokine gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleotide sequence coding for a chemokine protein or a functionally active analog or fragment or other derivative thereof, can be inserted into an appropriate expression vector, i.e., a vector which contains the necessary elements for the transcription and translation of the inserted protein-coding sequence. The necessary transcriptional and translational signals can also be supplied by the native chemokine gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a chemokine protein or peptide fragment may be regulated by a second nucleic acid sequence so that the chemokine protein or peptide is expressed in a host transformed with the recombinant DNA molecule. For example, expression of a chemokine protein may be controlled by any promoter/enhancer element known in the art. Promoters which may be used to control chemokine expression include, but are not limited to, the SV40 early promoter region, the promoter contained in the 3' long terminal repeat of Rous sarcoma virus, the herpes thymidine kinase promoter, the regulatory sequences of the metallothionein gene; prokaryotic expression vectors such as the β-lactamase promoter, or the tac promoter.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the chemokine protein(s), fragment(s), analogue(s), or derivative(s) may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric protein containing all or a portion of the chemokine is joined via a peptide bond to all or a portion of an antigen against which immunity is desired.

The chemokine protein(s) may also be isolated and purified by standard methods including chromatography (e.g., ion exchange, affinity, and sizing column chromatography), centrifugation, differential solubility, or by any other standard technique for the purification of proteins. The functional properties may be evaluated using any suitable assay. Alternatively, the protein can be synthesized by standard chemical methods known in the art.

In addition, chemokine proteins, derivatives (including fragments and chimeric proteins), and analogues can be chemically synthesized. For example, chemokines, derivatives and analogues can be synthesized by solid phase techniques, cleaved from the resin, and purified by preparative high performance liquid chromatography. Chemokines, derivatives and analogues that are proteins can also be synthesized by use of a peptide synthesizer. The composition of the synthetic peptides may be confirmed by amino acid analysis or sequencing.

The composition formulations of the invention comprise an effective immunizing amount of an immunologically active ingredient, i.e., one or more antigens, and an amount of one or more chemokine(s), or fragment(s) or derivative thereof, effective to enhance the immune response against the antigen in a subject, and a pharmaceutically acceptable carrier or excipient. Pharmaceutically acceptable carriers or excipients are well known in the art and include but are not limited to saline, buffered saline, dextrose, water, glycerol, ethanol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

In addition, if desired, the vaccine or composition preparation may also include minor amounts of auxiliary substances such as wetting or emulsifying agents, pH buffering agents, and/or an additional adjuvant which enhance the effectiveness of the vaccine or composition.

The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The chemokine(s), or fragment(s) or derivative(s) thereof, and/or the antigen(s) may be formulated into the composition as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

An effective dose (immunizing amount) is that amount sufficient to produce an immune response to the antigen(s) in the host to which the vaccine preparation is administered. The precise dose of the composition to be employed in the formulation will depend on the route of administration, and the nature of the subject to be immunized, and should be decided by the practitioner according to standard clinical techniques. Effective doses of the vaccines or compositions of the present invention may also be extrapolated from dose-response curves derived from animal model test systems.

Methods of introducing the composition may include oral, intracerebral, intradermal, intramuscular, intraperitoneal, intravenous, subcutaneous, intranasal or any other standard routes of immunization. The immune response of the test subjects can be analyzed by various approaches well known in the art, such as but not limited to: testing the reactivity of the resultant immune serum to the antigen of the chemokine-containing vaccine, as assayed by known techniques, e.g., immunosorbant assay (ELISA), immunoblots, radioimmunoprecipitations, etc.

EXAMPLES

The present invention relates to a method for directing an immune response in a subject comprising administering to the subject (i) an antigen or a nucleic acid encoding an antigen and (ii) a chemokine and/or functional equivalent thereof or a nucleic acid encoding a chemokine and/or functional equivalent of the chemokine.

In empirical work supporting the present application, the following four chemokines were compared:

RANTES (regulated on activation, normally T cell expressed and secreted), which has a broad chemoattractant activity, for T cells and monocytes/macrophages, as well as basophils, eosinophils, natural killer cells, mast cells and dendritic cells, but is unable to attract B cells. It functions through CCR-1, CCR-3, CCR-5 and CCR-9.

MCP-1 (monocyte chemotactic protein-1), which is chemoattractant for monocytes and T cells, as well as monocytes/macrophages, basophils, eosinophils, natural killer cells, mast cells and hematopoietic progenitor cells via the receptors CCR2B and CCR-9.

MDC (macrophage-derived chemoattractant), which causes chemotaxis of monocytes/macrophages, activated natural killer cells and dendritic cells by activating via CCR4, although there are indications that MDC also functions via other still unknown receptors.

BLC (B lymphocyte chemoattractant) is involved mostly in chemotaxis of B lymphocytes. It induces the formation of germinal centers by directing B cells to follicles of secondary lymphoid tissues and functions via CXCR5 (BLR-1 or BCA-1).

The receptor-specificity, cellular expression patterns and their chemoattractant are set forth in the following table 2:

TABLE 1

Chemokines used for immunizations, their classes, receptors, sources and target cells.

| Chemokine | Class | Receptor | Source | Target Cells |
|---|---|---|---|---|
| BLC/BCA-1 | CXC (α) | CXCR5 | Liver, Spleen, lymph node | B |
| MCP-1 | CC (β) | CCR2 | F, M, L, EC, EP, tumor cell lines | M, T, E, Ba, NK, HPC, MC |
| MDC | CC (β) | CCR4 | DC, M, T | DC, M, NK |
| RANTES | CC (β) | CCR1, CCR3, CCR5 | F, M, T, ME, various cell lines | M, T, Ba, E, NK, MC, DC |

Abbreviations:
I) the chemokines: BLC/BCA-1, B-cell attracting chemokine; MCP-1, monocyte chemoattractant protein-1; MDC, macrophage derived chemokine; RANTES: regulated upon activation, normal T cell expressed and secreted;
II) the sources/target cells: B, B lymphocytes; Ba, Basophils; DC, Dentritic Cells; E, Eosinophils, F, Fibroblasts; HPC, Hemotopoietic Progenitor Cells, M, Monocytes/Macrophages; MC, Mast Cells; ME, Mesangial Cells; N, Neutrophils; T, T lymphocytes.

Chemokine Nucleic and Amino Acid Sequence and Functional Equivalents

The chemokine amino acid and nucleic acid sequences used in the methods and compositions of the invention can be obtained by any method known in the art. Chemokine nucleotide and amino acid sequences for humans and other animals are publicly available in public databases and applicable for use herein. For examples the Genbank Accession Nos. for MDC; MCP-1; RANTES; and BLC are set forth below in Table 3.

```
Homo sapiens       U83171         1 gagacataca ggacagagca tggctcgcct acagactgca ctcctggttg tcctcgtcct macrophage-                      61 ccttgctgtg gcgcttcaag caactgaggc aggcccctac ggcgccaaca tggaagacag derived                         121 cgtctgctgc cgtgattacg tccgttaccg tctgcccctg cgcgtggtga aacacttcta chemokine                       181 ctggacctca gactcctgcc cgaggcctgg cgtggtgttg ctaaccttca gggataagga (MDC)                           241 gatctgtgcc gatcccagag tgccctgggt gaagatgatt ctcaataagc tgagccaatg SEQ ID NO: 1                    301 aagagcctac tctgatgacc gtggccttgg ctcctccagg aaggctcagg agccctacct 361 ccctgccatt atagctgctc cccgccagaa gcctgtgcca actctctgca ttccctgatc 421 tccatccctg tggctgtcac ccttggtcac ctccgtgctg tcactgccat ctcccccctg 481 accctctaa cccatcctct gcctccctcc ctgcagtcag agggtcctgt tcccatcagc 541 gattcccctg cttaaaccct tccatgactc cccactgccc taagctgagg tcagtctccc 601 aagcctggca tgtggccctc tggatctggg ttccatctct gtctccagcc tgcccacttc 661 ccttcatgaa tgttgggttc tagctccctg ttctccaaac ccatactaca catcccactt 721 ctgggtcttt gcctgggatg ttgctgacac tcagaaagtc ccaccacctg cacatgtgta 781 gccccaccag ccctccaagg cattgctcgc ccaagcagct ggtaattcca tttcatgtat 841 tagatgtccc ctggccctct gtccctctt aataaccta gtcacagtct ccgcagattc 901 ttgggatttg ggggttttct cccccacctc tccactagtt ggaccaaggt ttctagctaa 961 gttactctag tctccaagcc tctagcatag agcactgcag acaggccctg gctcagaatc
```

-continued

```
1021 agagcccaga aagtggctgc agacaaaatc aataaaacta atgtccctcc cctctccctg
1081 ccaaaaggca gttacatatc aatacagaga ctcaaggtca ctagaaatgg gccagctggg
1141 tcaatgtgaa gccccaaatt tgcccagatt cacctttctt cccccactcc cttttttttt
1201 tttttttttt tgagatggag tttcgctctt gtcacccacg ctggagtgca atggtgtggt
1261 cttggcttat tgaagcctct gcctcctggg ttcaagtgat tctcttgcct cagcctcctg
1321 agtagctggg attacaggtt cctgctacca cgcccagcta attttttgtat ttttagtaga
1381 gacgaggctt caccatgttg gccaggctgg tctcgaactc ctgtcctcag gtaatccgcc
1441 cacctcagcc tcccaaagtg ctgggattac aggcgtgagc cacagtgcct ggcctcttcc
1501 ctctccccac tgccccccc aacttttttt ttttttttat ggcagggtct cactctgtcg
1561 cccaggctgg agtgcagtgg cgtgatctcg gctcactaca acctcgacct cctgggttca
1621 agtgattctc ccaccccagc ctcccaagta gctgggatta caggtgtgtg ccactacggc
1681 tggctaattt ttgtattttt agtagagaca ggtttcacca tattggccag gctggtcttg
1741 aactcctgac ctcaagtgat ccaccttcct tgtgctccca aagtgctgag attacaggcg
1801 tgagctatca cacccagcct ccccctttt ttcctaatag gagactcctg tacctttctt
1861 cgttttacct atgtgtcgtg tctgcttaca tttccttctc ccctcaggct ttttttgggt
1921 ggtcctccaa cctccaatac ccaggcctgg cctcttcaga gtaccccca ttccactttc
1981 cctgcctcct tccttaaata gctgacaatc aaattcatgc tatggtgtga aagactacct
2041 ttgacttggt attataagct ggagttatat atgtatttga aaacagagta aatacttaag
2101 aggccaaata gatgaatgga agaattttag gaactgtgag aggggacaa ggtgaagctt
2161 tcctggccct gggaggaagc tggctgtggt agcgtagcgc tctctctctc tgtctgtggc
2221 aggagccaaa gagtagggtg taattgagtg aaggaatcct gggtagagac cattctcagg
2281 tggttgggcc aggctaaaga ctgggagttg ggtctatcta tgcctttctg gctgattttt
2341 gtagagacgg ggttttgcca tgttacccag gctggtctca aactcctggg ctcaagcgat
2401 cctcctggct cagcctccca aagtgctggg attacaggcg tgaatcactg cgcctggctt
2461 cctcttcctc ttgagaaata ttcttttcat acagcaagta tgggacagca gtgtcccagg
2521 taaaggacat aaatgttaca agtgtctggt cctttctgag ggaggctggt gccgctctgc
2581 agggtatttg aacctgtgga attggaggag gccatttcac tccctgaacc cagcctgaca
2641 aatcacagtg agaatgttca ccttataggc ttgctgtggg gctcaggttg aaagtgtggg
2701 gagtgacact gcctaggcat ccagctcagt gtcatccagg gcctgtgtcc ctcccgaacc
2761 cagggtcaac ctgcctgcca caggcactag aaggacgaat ctgcctactg cccatgaacg
2821 gggccctcaa gcgtcctggg atctccttct ccctcctgtc ctgtccttgc ccctcaggac
2881 tgctggaaaa taaatccttt aaaatagtaa aaaaaaaaaa aaa
```

Homo sapiens x14768 monocyte chemoattractant protein 1 (MCP-1) SEQ ID NO: 2

```
  1 ctaacccaga aacatccaat tctcaaactg aagctcgcac tctcgcctcc agcatgaaag
 61 tctctgccgc ccttctgtgc ctgctgctca tagcagccac cttcattccc caagggctcg
121 ctcagccaga tgcaatcaat gccccagtca cctgctgtta aacttcacc aataggaaga
181 tctcagtgca gaggctcgcg agctatagaa gaatcaccag cagcaagtgt cccaaagaag
241 ctgtgatctt caagaccatt gtggccaagg agatctgtgc tgaccccaag cagaagtggg
301 ttcaggattc catggaccac ctggacaagc aaacccaaac tccgaagact gaacactca
361 ctccacaacc caagaatctg cagctaactt attttcccct agctttcccc agacacctg
421 ttttatttta ttataatgaa ttttgtttgt tgatgtgaaa cattatgcct taagtaatgt
```

```
                                          -continued
                             481 taattcttat ttaagttatt gatgttttaa gtttatcttt catggtacta gtgttttta 541 gatacagaga cttggggaaa ttgcttttcc tcttgaacca cagttctacc cctgggatgt 601 tttgagggtc tttgcaagaa tcattaatac aaagaatttt ttttaacatt ccaatgcatt 661 gctaaaatat tattgtggaa atgaatattt tgtaactatt acaccaaata aatatatttt 721 tgtac Homo sapiens   AF266753        1 atgaaggtct ccgcggcacg cctcgctgtc atcctcattg ttactgccct ctgcgctcct RANTES         see also       61 gcatctgcct ccccatattc ctcggacacc acaccctgct gctttgccta cattgcccgc SEQ ID NO: 3   AW769950      121 ccactgcccc gtgcccacat caaggagtat ttctacacca gtggcaagtg ctccaaccca 181 gcagtcgtct ttgtcacccg aaagaaccgc caagtgtgtg ccaacccaga gaagaaatgg 241 gttcgggagt acatcaactc tttggagatg agctag Homo sapiens B AJ002211        1 cagagctcaa gtctgaactc tacctccaga cagaatgaag ttcatctcga catctctgct cell-attracting               61 tctcatgctg ctggtcagca gcctctctcc agtccaaggt gttctggagg tctattacac chemokine                    121 aagcttgagg tgtagatgtg tccaagagag ctcagtcttt atccctagac gcttcattga (BLC)                        181 tcgaattcaa atcttgcccc gtgggaatgg ttgtccaaga aaagaaatca tagtctggaa SEQ ID NO: 4                 241 gaagaacaag tcaattgtgt gtgtggaccc tcaagctgaa tggatacaaa gaatgatgga 301 agtattgaga aaagaagtt cttcaactct accagttcca gtgtttaaga gaaagattcc 361 ctgatgctga tatttccact aagaacacct gcattcttcc cttatccctg ctctgggatt 421 ttagttttgt gcttagttaa atcttttcca gggagaaaga acttccccat acaaataagg 481 catgaggact atgtaaaaat aaccttgcag gagctggatg gggggccaaa ctcaagcttc 541 tttcactcca caggcaccct attntacact tgggggtttt gcnttctttn tttcntcagg 601 gggggggaaa gtttcttttg gaaantagtt nttccagttn ttaggtatta cagggttntt 661 ttt
```

Materials and Methods

Plasmids Used and their Production for DNA Vaccinations

DNA plasmids carrying the HIV-1$_{BaL}$ envelope genes encoding for modified and codon-optimized glycoproteins gp120 or gp160 (Midland Certified Reagents, Midland, Tex.), were cloned into the pcDNA3.1 expression vector (Invitrogen, Inc., San Diego, Calif.) and expressed under control of cytomegalovirus promoter (pcDNA3.1(zeo)$_{BaL}$gp120 or $_{BaL}$gp160). Similarly, the genes encoding the murine chemokines BLC, MCP-1 and RANTES were cloned into the same vector (pcDNAmuBLC, pcDNAmuMCP-1 and pcDNAmuRANTES). Plasmid DNA for injection was prepared endotoxin-free (<0.5 EU/ml, as detected by limulus amoebocyte lysate assay [BioWhittaker, Walkersville, Md.] using EndoFree Giga kits [Qiagen, Santa Clara, Calif.]).

Mice, Immunization Regimen and Serum Sample Collection

Female Balb/c mice (H-2$^d$, 6-8-week-old) (Charles River Laboratories, Wilmington, Mass.) were injected 3× intramuscularly (i.m.) into each quadricep on a biweekly basis with 100 µg of plasmid DNA encoding equal amounts of one of the chemokines or the vector pcDNA3.1 and pcDNAgp120 or pcDNAgp160, respectively. Serum samples were taken prior to each injection and 3 and 6 weeks after the final injection. Eleven days prior to the first DNA injection, an i.m. injection of 50 µl of 10 µM snake cardiotoxin (Sigma, St Louis, Mo.) in each quadricep was performed.

Serum Antibody (Ab) Assays

To monitor the development of the specific Ab response against HIV-1$_{BaL}$gp160 or HIV-1$_{BaL}$gp120 in the DNA vaccination assays, serum samples were analyzed using an anti-gp120-specific capture-ELISA. Briefly, a 96-well Maxisorp ELISA plate (Nunc, Naperville, Ill.) was coated overnight with 100 µl of 2 µg/ml anti-HIV-1$_{BaL}$gp120 capture Ab (D7234, International Enzymes, Inc, Fallbrook, Calif.) at 4° C., washed 4× with PBS-0.5% Tween-20, blocked with 200 µl of 5% skim milk powder in PBS (5% blotto) for 1 h at room temperature, washed again and loaded with 150 ng/ml recombinant gp140 (rgp140) in 2% blotto for 1 h at room temperature. After washing again, incubation at room temperature was performed for 1 h with serially diluted sera of the DNA vaccinated mice (heat-inactivated for 30 min at 56° C.) starting at 1/20 in PBS containing 2% skimmed milk powder (blotto) and 5% sheep serum. The plate was washed and incubated with 1 µg/ml of horseradish peroxidase (HP) conjugated affinity-purified and serum adsorbed goat anti-mouse secondary Ab (Kierkegaard & Perry Laboratories (KPL), Gaithersburg, Md.) for 1 h at room temperature and then washed. The plate was developed with 100 µl tetramethylbenzidine (TMB; KPL) for 5-10 min, stopped with 50 µl 1N H$_2$SO$_4$ and analyzed at 450 nm with a Victor plate reader (Wallac, Turku, Finland).

Subtyping of the Abs in order to determine the Th-type of the immune response was conducted on sera pooled from four to six animals per group using the same protocol, but replacing the secondary anti-total IgG Ab-mix with either IgG1-HRP or IgG2a-HRP goat anti-mouse Abs (KPL), starting with a 1:12.5 dilution.

T-Cell Proliferation/Restimulation Assays

An erythrocyte-depleted splenocyte suspension (n=2) was washed several times with and resuspended in complete RPMI 1640 medium (supplemented with 10% fetal bovine serum (FBS), 2 mM L-glutamine, 10 mM 2-mercaptoethanol, 10 mM HEPES, 10 mM penicillin/streptomycin, 10 mM sodium pyruvate and 30 U/ml human interleukin-2 (hIL-2) (Genzyme Molecular Oncology, Framingham, Mass.)). Splenocytes were cultured immediately in triplicate ($10^6$ cells per well in 100 µl) in 96-well flat-bottom microtiter plates, stimulated with rgp160 protein (1 µg/ml; HIV-$1_{BaL}$; Peprotech, Rocky Hill, N.J.) and incubated at 37° C. with 5% $CO_2$ for 72 h. Proliferation was measured in triplicate by incorporation of tritiated thymidine ([$^3$H]-T) by addition of 1 µCi [$^3$H]-T and incubation for another 18 h. The plate was harvested and the amount of [$^3$H]-T was measured in a β-plate reader (Wallac). Complete RPMI medium (with 10% FBS and 30 U/ml hIL-2) served as a control. Stimulation with 5 µg/ml of the polyclonal stimulator phytohemagglutinin (PHA; Sigma) served as a positive control.

Th1- and Th2-type Cytokine ELISA Assays

In order to determine the Th pattern of the immune response induced by the immunogen and the co-administered chemokines, supernatants of effector cell cultures were tested for murine Th1-type cytokine IFN-γ and Th2-type cytokine Il-4. Splenocytes (10×$10^6$) from the experimental animals were cultured for 72 h with 1 µg/ml rgp160 in a total volume of 1 ml of complete culture medium (as described above) in a 48-well tissue culture plate. The supernatants were harvested and assayed for the presence of IFN-γ and Il-4 using ELISA kits according to the manufacturer's protocol (R&D Systems, Minneapolis, Minn.). Antigen-specific cytokine secretion was obtained by subtracting the cytokine content of splenocytes incubated with complete medium alone.

Evaluation of CD8+T Cells by the IFN-γ Enzyme-Linked Immunospot (ELISpot) Assay

The ELISpot assay to detect antigen-specific CD8$^+$T cells was performed as reported by Miyahira et al. [15]. Briefly, 6 weeks after the third injection two mice were sacrificed and a single-cell suspension was prepared from the two pooled spleens. The erythrocyte-depleted cells were resuspended in 5 ml complete culture medium (see above) supplemented with 30 U/ml hIL-2 and cultured as bulk in a 6-well plate at a concentration of 5×$10^6$/ml for 6 days in the presence of 0.5×$10^6$ of P815 cells, which had been irradiated with 10,000 Rad in a Gamma cell irradiator and loaded with 10 µg/ml peptide V3 (HIV-1 MN, residues 299-331, relevant H-2d MHC class I restricted peptide, NovaBiochem, Laeufelfingen, Switzerland) for >2 h at 4° C. At Day 5, a Millipore HA ELISpot Multiscreen 96-Filtration-ELISpot plate (Millipore, S. A., Molsheim, France) was coated overnight at room temperature with 100 µl of 5 µg/ml anti-IFN-γ(Clone # 18181D; Pharmingen, San Diego, Calif.) in PBS. At Day 6 the plate was washed with PBS and blocked with 200 µl complete medium for >30 min at 37° C. Meanwhile, fresh P815 cells were pulsed with the MHC-I restricted relevant peptide V3 for >2 h at 4° C. and then added to the ELISpot plate at a ratio of effector splenocytes (1×$10^6$) to target P815 cells of 10:1 in a total volume of 100 µl per well fresh, complete medium. As a negative control, effector splenocytes were cultivated in medium only, whereas the positive control contained splenocytes from mice who were intraperitoneally injected with 5×$10^6$ P815 cells 7 days prior to spleen removal. The ELISpot plate was incubated for 24 h at 37° C., and then washed 2× with PBS, once with $dH_2O$ and 2× with PBS-Tween-20 (0.05%). The plate was incubated with 100 µl anti-IFN-γ (2 µg/ml; Clone #18112D; Pharmingen) in 0.05% PBS-Tween-20 and 1% FBS for 2 h at room temperature. The plate was washed 4× with 0.05% PBS-Tween-20 and 100 µl of ExtrAvidin-alkaline phosphatase (Sigma; diluted 1/2000 in PBS-Tween-20 and 1% FBS) was added per well, followed by a 2 h incubation at room temperature. The plate is then washed 3× with 0.05% PBS-Tween-20 and 200 µl of freshly prepared 5-bromo-4-chloro-3-indolyl phosphate/nitroblue tetrazolium (BCIP/NBT) substrate buffer (Sigma). The spots in each well were counted using a dissection light microscope.

Statistical Analysis

Significance analysis between results, obtained from various groups of mice, was performed by using the paired Student's t-test and GraphPad software. Probability values of >0.05 were considered insignificant.

Results

In order to investigate the effect of select chemokines on the immune response triggered by DNA-based immunization, expression constructs encoding for one of the chemokines, BLC, MCP-1 or RANTES (or the empty vector pcDNA3.1 as a control), along with plasmids expressing either the soluble HIV-$1_{BaL}$ envelope antigen gp120 or the membrane-bound antigen gp160, respectively, were injected three times biweekly into the leg muscle of Balb/c mice and investigated the changes in the immune response.

Humoral Responses

Serum antibody ELISA was used to assess the development of the humoral immune response. An arbitrary value was chosen equal to 2.5× the assay background to calculate endpoint titers. It was observed that under our DNA-based immunization regimen, high titers of antigen-specific antibodies were induced after two inoculations, although with sharp differences in titers between different antigens. When using gp120-expressing DNA vector as immunogen, endpoint titers reached 1/250,000 (FIG. 1), while the gp160-expressing construct was less efficient in triggering antibodies, reaching a peak endpoint titer of about 7500 (FIG. 1) after as many inoculations. In addition, the titers of antigen-specific antibodies tended to decrease, as expected, 5 weeks past the last immunization in gp160-immunized animals, which resulted (except in the case of the RANTES-co-injected group) in a bell-shaped curve. Conversely, the groups that were co-injected along with the antigen gp120 displayed a sustained response with antibody titer levels, reaching a plateau 4 weeks after the initial immunization (FIG. 1). A dichotomy was observed when the antigen-expressing and chemokine-expressing constructs were co-injected. In the case of gp160-immunized animals, co-injection of chemokine genes resulted in antibody titers that were lower as compared to these obtained with the immunogen alone. This phenomenon was particularly dramatic when the RANTES-expressing construct was used. In the gp120-immunized group, co-injection of BLC or MCP-1 chemokine-expressing constructs resulted in antigen-specific antibody levels comparable to those obtained with antigen alone. However, decreased antibody levels were detected in RANTES-co-injected animals as compared to the antigen alone group.

Ratio of Immunoglobulins (Ig) IgG1 to IgG2a

Figure 2:
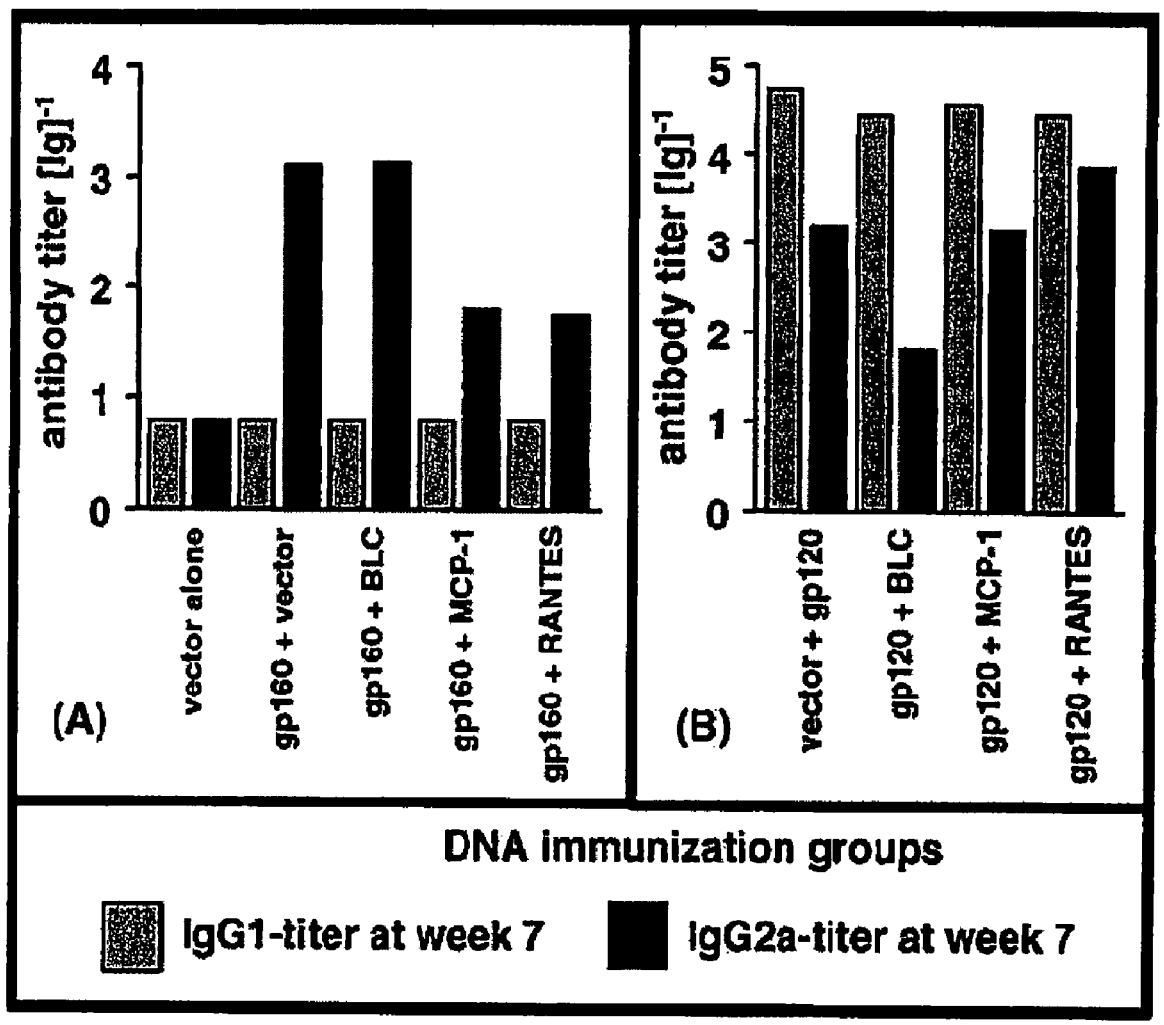
FIG. 2 shows that DNA vaccines induce different patterns of Ab-isotypes, which can be further altered by chemokine co-administration. Six 8-week-old BALB/c mice were immunized 3× at Weeks 0, 2 and 4 with either plasmid-derived chemokine BLC, MCP-1 or RANTES or the control vector and either DNA vaccine encoding for HIV-1$_{BaL}$gp160 (AgA) or HIV-1$_{BaL}$gp120 (AgB). At Week 7, IgG1 and IgG2a titers were measured by a vaccine-specific (anti-gp140) capture-ELISA. Results are expressed as mean vaccine-specific antibody titers (in $\log_{10}$) obtained from sera pooled from four to six immunized mice for each immunization group.

The ratio of the antigen-specific serum immunoglobulin subtypes IgG1 to IgG2a can be used as an indirect marker for the Th-type association of an immune response; the production of the Ig-isotype IgG1 is more typically associated to a Th2 response, while the Ig-isotype IgG2a is considered to be associated with Th1 responses [16] and [17]. Thus, the IgG1/IGg2a profile of the antibody response was analyzed using an ELISA-based approach, on sera pooled from four to six animals in each immunization group. The comparison of the two DNA-based immunogens HIV-1$_{BaL}$gp160 and HIV-1$_{BaL}$gp120 demonstrated that only the latter induced detectable titers of the IgG1-isotype. In the groups that received gp160 as antigen, the IgG1-isotype could not be detected and had been given the arbitrary value of half of the lowest serum dilution (i.e. 6.25). In comparison, the subtype IgG2a was detected and clearly elicited by gp160 (FIG. 2A). Co-injection of DNA encoding for MCP-1 and RANTES with the gp160 construct reduced the levels of circulating IgG2a antibodies by more than 10-fold, unlike when BLC was used (FIG. 2A). In contrast, all groups receiving DNA-encoded gp120 induced similar, high levels of IgG1, whereas the levels of IgG2a were altered by the co-injection of chemokine DNA: BLC-co-injection was associated with the lowest levels of IgG2a, which were more than 25 times less than the vaccine gp120 alone (62, as compared to 1562), while RANTES gene co-injection was associated with an induction of the IgG2a-isotype, increasing the titer by almost half a log (from 1562 to 7200) over the group which received the gp120-expressing construct alone (FIG. 2B). MCP-1 did not alter the isotype profile in the context of gp120 responses (FIG. 2B).

Antigen-Induced Proliferation

Figure 3:
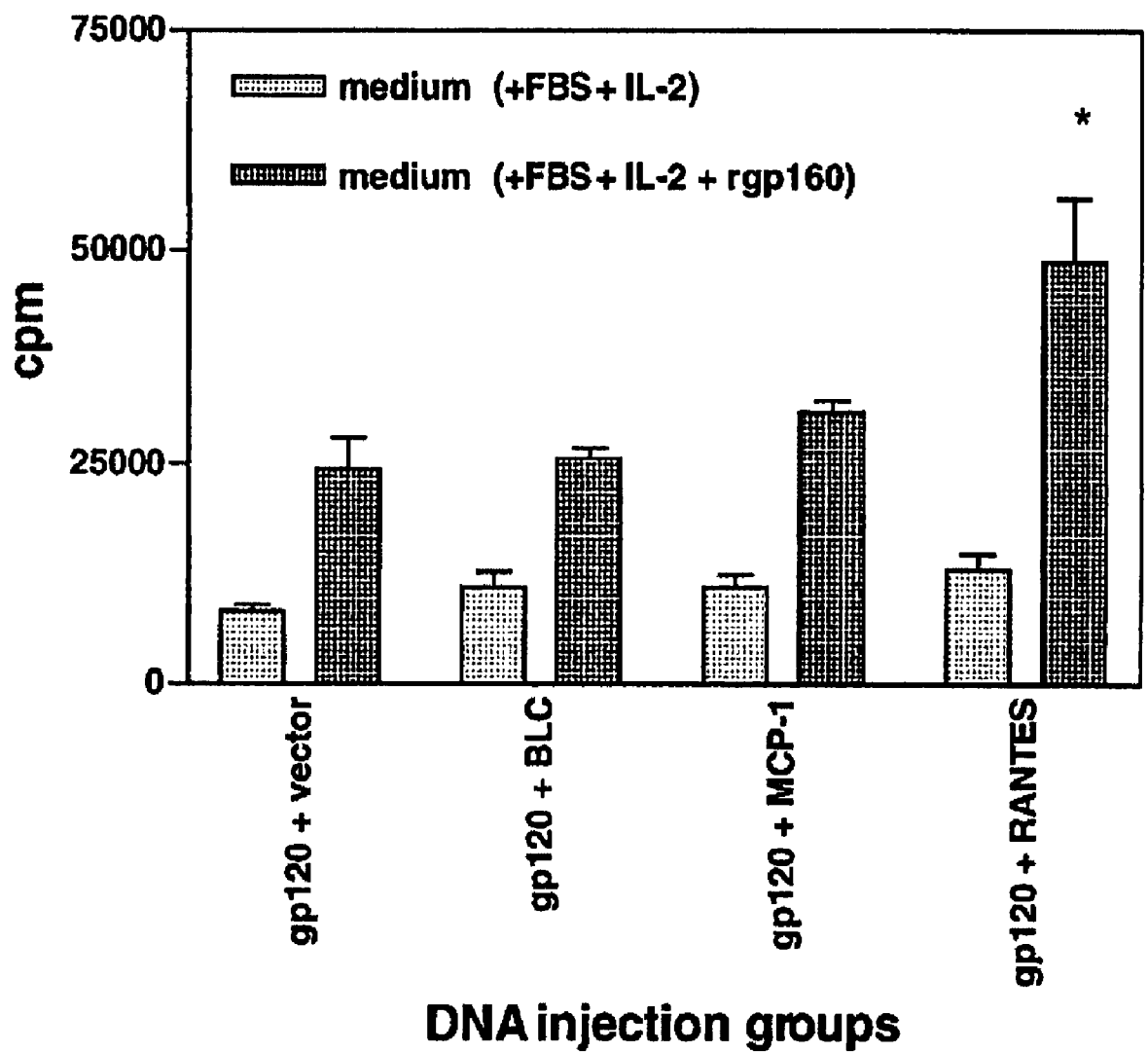
FIG. 3 shows thymidine uptake in splenocytes after in vitro restimulation with rgp160 protein. Each group was immunized with 100 μg per leg of HIV-1$_{BaL}$gp120 and the same amount of BLC or MCP-1 or RANTES DNA at Weeks 0, 2 and 4. Six weeks after the last injection, two mice were sacrificed, and spleen cells were pooled. Splenocytes were then stimulated with 1 μg/ml gp160 and 5 ρg/ml PHA as a positive control. As a negative control, splenocytes were cultures in medium alone, containing 30 U/ml hIL-2 and 10% FBS as a source of irrelevant protein. After 3 days of stimulation, 1 μCi of tritiated thymidine was added for 18 h and then the cells were harvested and cpm was determined. Samples were assayed in triplicate. The assay was repeated at least three times with similar results. (*) Statistically significant compared to specific stimulation of gp120 alone ($P<0.05$), using paired Student's t-test.

Chemokines can play an important role in the activation of polyclonal and antigen-specific helper T cells during the induction of an immune response [18]. Therefore, the effect of co-injected chemokine-expressing DNA on the immunogenicity of gp120 and gp160 DNA vaccines was investigated in the context of antigen-specific splenocyte proliferation, a surrogate marker of helper activity. Recombinant HIV-1$_{BaL}$gp160 protein (1 μg/ml) was used to assess antigen specific stimulation of T cells. PHA (5 μg/ml), a polyclonal stimulator, was used as a positive control. Interestingly, only gp120-, but not gp160-DNA vaccinated animals showed a significantly increased antigen-induced proliferative response, as compared to control animals, injected with the vector (FIG. 3). Moreover, the co-injection of RANTES DNA was associated with a further, significant increase in the thymidine uptake as compared to the group that received gp120 alone (FIG. 3).

Cytokine Production

Figure 4:
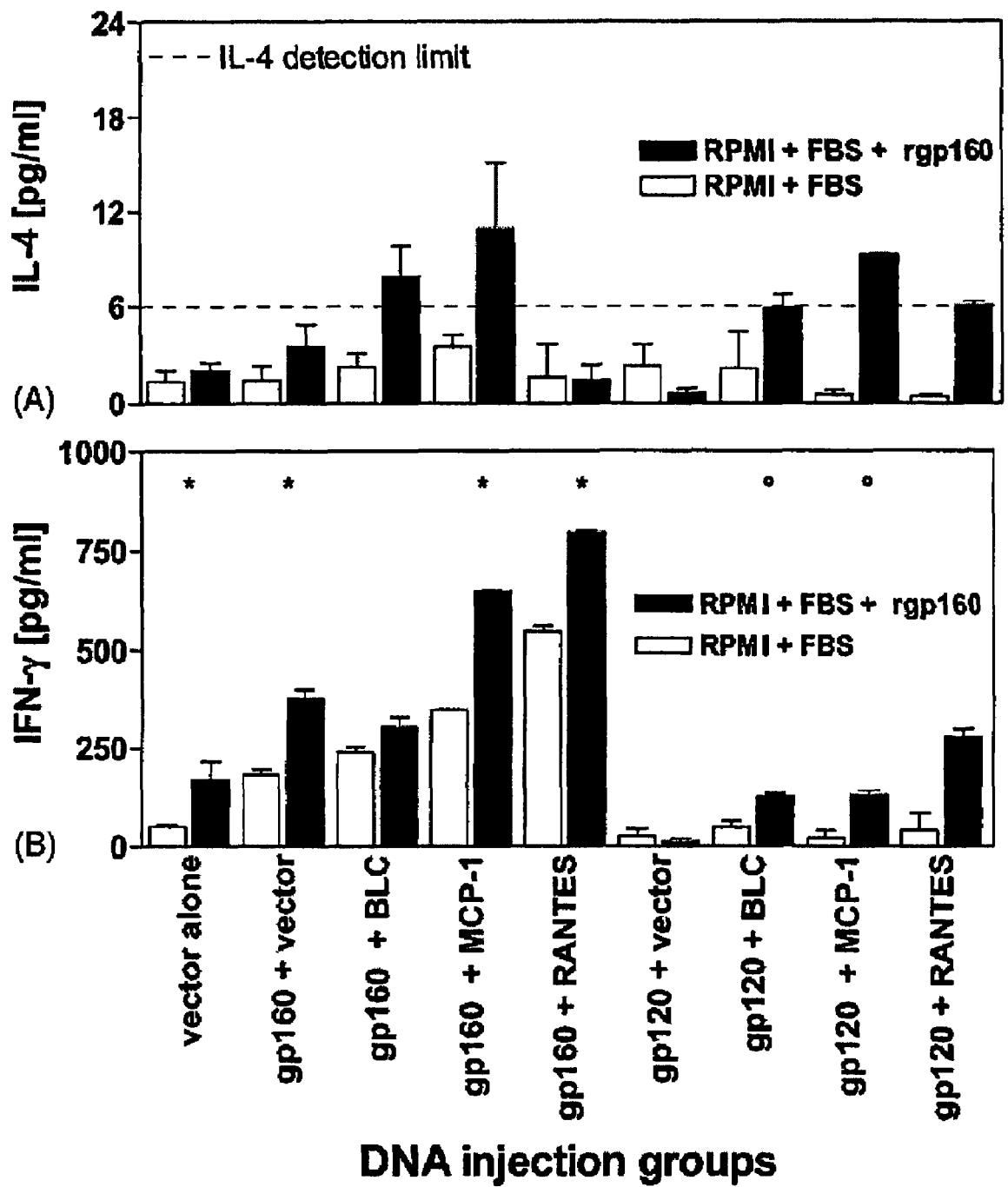
FIG. 4 shows cytokine ELISA of supernatants from antigen (gp160 and gp120) and chemokine-DNA immunized splenocyte cultures. Prior to splenocyte culturing at Week 10, mice were immunized 3× (at Weeks 0, 2 and 4) into each quadricep with 100 μg DNA, equally distributed between antigen expression plasmid and chemokine expression plasmid or control vector (V). The erythrocyte-depleted splenocytes of two mice were pooled and stimulated with 1 μg/ml of gp160 protein for 3 days. The cell-free supernatants were tested for Il-4 (Panel A) and IFN-γ (Panel B) expression, respectively. The injected plasmid combinations are represented on the x-axis; the y-axis displays the cytokine levels in pg/ml. (*) Significant difference as compared to nonspecific challenge with FBS (P<0.05). The experiment was repeated 3× with similar results.

The Th-type of a polarized immune response is associated with expression patterns of certain marker cytokines [19] and [20]. Accordingly, IFN-γ together with IL-2, are considered the key cytokines for Th1-type immune responses, i.e. directed towards cellular responses. IL-4, together with IL-5 and IL-10, are considered the hallmark cytokines for Th2 responses, being associated with humoral immunity. Therefore, the cytokine profiles elicited in response to co-injection with chemokine and envelope DNA was examined (FIG. 4). As in the case of other parameters, a dichotomy was observed in the antigen-induced cytokine responses in animals immunized with gp120- as compared to those injected with gp160-expressing constructs. In general, antigen-induced production of IFN-γ was markedly higher in animals that were immunized with gp160 DNA as compared to those immunized with gp120 DNA. Co-injection of expression constructs encoding for chemokines MCP-1 or RANTES were found to be associated with a significant increase in IFN-γ production from cultured splenocytes, in both gp120- and gp160-immunized groups; RANTES was the best inducer in both groups in terms of absolute levels, but when background levels were subtracted, MCP-1 was associated with the best induction of IFN-γ in gp160-, but not gp120-immunized animals. In contrast, co-injection of the expression constructs encoding for BLC and gp160 was found to be associated with significantly lower production of IFN-γ from splenocytes, as compared to injection of the DNA-based antigen alone. Instead, when gp120 was used as immunogen, co-injection with BLC induced significantly higher levels of IFN-γ than the vaccine alone. Nevertheless, the amounts of IFN-γ produced in all groups of mice injected with the gp120 antigen (with or without chemokine co-injection) were markedly less than those attained in mice injected with gp160 alone.

Antigen-induced IL-4 levels were generally below detectable limits in animals immunized with either gp120- and gp160-expressing constructs and could be detected at very low levels (<15 μg/ml) only in animals that were co-injected with either BLC or MCP-1 (FIG. 4A), but not with RANTES.

Figure 5:
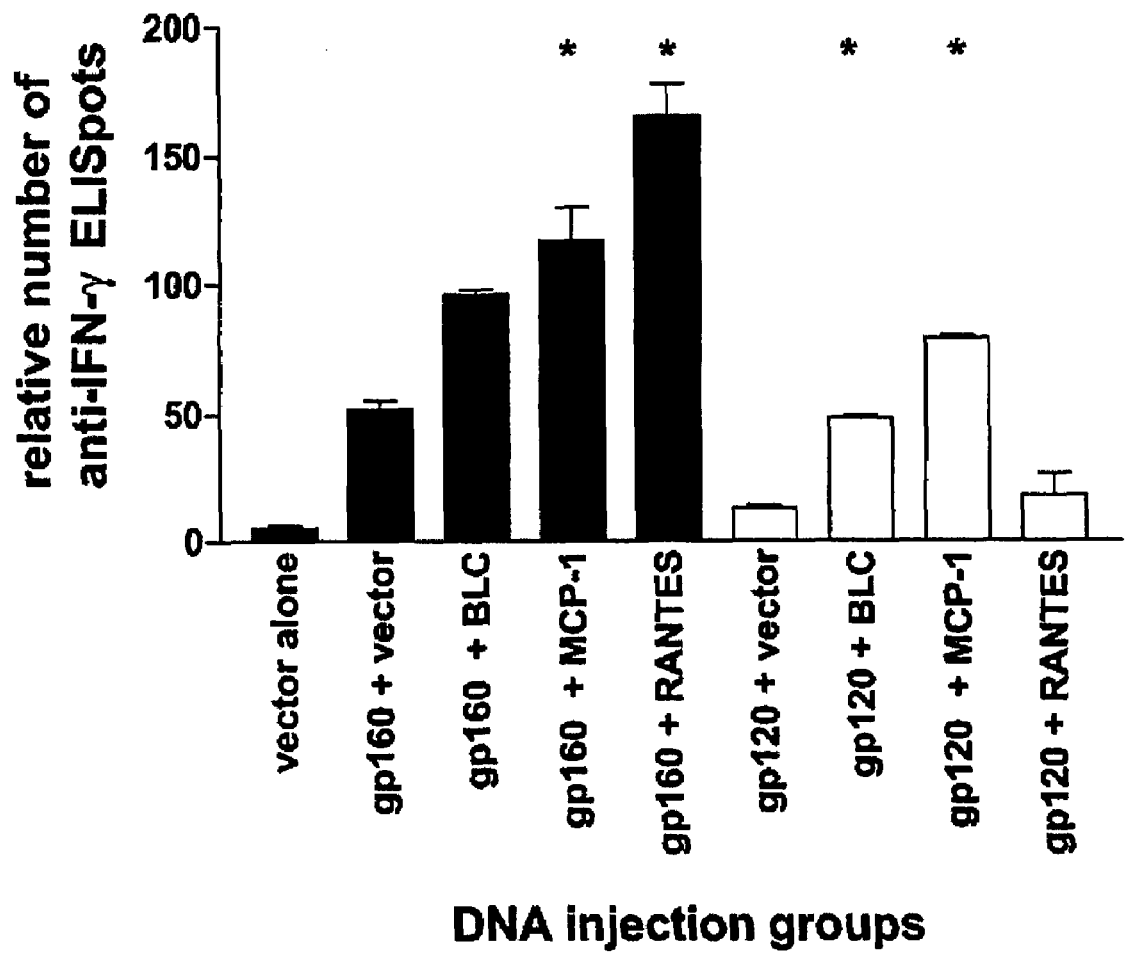
FIG. 5 shows number of IFN-γ secreting cells as determined by ELISpot assay. After injecting groups of 6 mice 3× at Weeks 0, 2 and 4 with 100 µg DNA per leg with different combinations of antigens (Ag), [either HIV-1$_{BaL}$gp160 (filled bars) or HIV-1$_{BaL}$gp120 (open bars)], and different chemokines (BLC, MCP-1, or RANTES), or control DNA, respectively, splenocytes were recovered at Week 13 and pooled (n=2). Single-cell suspensions were diluted to $4\times10^6$/ml and were cultured in the presence of the same number of irradiated P815 stimulator cells for 6 days in 5 ml complete RPMI (substituted with 10% FBS, Per/Strep, Glutamine, HEPES, Na Pyruvate and 2-ME). Then, $1\times10^6$ effector-splenocytes were challenged with V3$_{BaL}$-peptide pulsed P815-stimulator cells at a ratio 3:1 in 200 µl RPMI in anti-IFN-γ-coated Millipore HA ELISpot plates overnight at 37° C. The following day, the number of IFN-γ secreting cells, or the number of spots, respectively, were counted in each well after washing out the cells, incubating with streptavidine-conjugated anti-IFN-γ Abs for 2 h, incubating with the substrate for 2 h and waiting for the major spots to develop (5-10 min). Results are displayed as the relative number of appearing spots equal to number of spots in the presence, minus the number of spots in the absence of V3$_{BaL}$peptide.

Effect of Chemokine-Plasmid Co-Injection Along with HIV-Vaccines on the Cellular Response In order to evaluate whether select chemokines can enhance cell mediated immunity, the number of antigen-specific IFN-γ secreting cells, detected by ELISpot assay, was used as a marker for the cellular immune response [21] and [22]. When splenocytes were incubated 6 weeks after the third DNA injection with a specific peptide of the V3-loop of the HIV-1$_{BaL}$gp120 protein, it was found that the responses to the HIV-1$_{BaL}$gp160 and the secreted antigen HIV-1$_{BaL}$gp120 were notably different. The overall numbers of antigen specific ELISpots were significantly higher in the groups co-injected with HIV-1$_{BaL}$gp160 than these observed in the groups co-injected with gp120 (FIG. 5). Similar to other observations with other immune response parameters, co-injection of constructs expressing chemokines BLC, MCP-1 and RANTES was associated with different responses according to the immunogens that were used. Co-injection of MCP-1 induced a significant increase in the IFN-γ secreting cell numbers in animals co-injected with either gp120 (>6-fold; P=0.016) or gp160 (>2-fold; P=0.0079; FIG. 5). BLC induced a significant increase in the number of ELISpots over the antigen alone group only when gp120 was co-administered as immunogen (4-fold; P=0.015), not in combination with gp160 (FIG. 5). Conversely, the RANTES expression construct induced a significant increase only when co-injected along with gp160, not gp120, yielding the highest number of ELISpots of all groups in conjunction with gp160 DNA (more than 3-fold as compared to the antigen alone; P=0.002847), but the lowest number of all chemokine-co-injected groups in conjunction with gp120 DNA (no increase over antigen alone; FIG. 5).

Discussion

Chemokines, which play a central role in determining the nature of immune responses, are shown herein to deliberately modulate immune responses. Further, the capacity of certain chemokines to selectively recruit specific cell subsets selectively can be exploited to bias the immune responses toward Th1- versus Th2-type patterns or vice versa.

The impact of co-injecting select chemokine genes and target antigen genes was investigated on responses elicited by DNA vaccines. HIV envelope antigens encoded by human codon optimized genes were used that enable high level expression in mammalian cells as immunogens. RANTES was selected because its receptors, CCR1, CCR3, and CCR5 are expressed on a variety of cells prevalently associated with Th1 responses [4], MCP-1 because it is a potent chemoattractant of antigen presenting cells such as monocytes and DC via CCR2, and BCL because its receptor, CXCR5, is almost exclusively expressed on B cells [4]. Therefore, these chemokines targeted a distinct cell subpopulation and it has been shown herein induce differential modulation of immune responses.

Qualitative differences were expected in the immune responses to gp120 versus gp160 due to the different cellular localization of these antigens. gp160, being membrane bound via its transmembrane domain, is more likely to induce a cellular response, whereas gp120, being a soluble antigen, was expected to preferentially generate humoral response [29] and [30]. In the specific case of intramuscular DNA vaccines, optimal induction of humoral immune responses requires the active secretion of antigen [30], which is likely to be less efficient in the gp160-expressing construct, as compared to the gp120 construct. Accordingly, it was observed that the membrane-bound gp160 induced weaker humoral response under all conditions/with all chemokines, as compared to soluble gp120 as shown in FIG. 5. Unexpectedly, especially with regard to BLC, enhancement of antibody titers using chemokines was not observed. This apparent lack of effect could be due to the need for doses of DNA encoding for chemokines higher than those used in this study. In alternative, it is possible that the strategy of coinjecting chemokine and antigen contemporarily might not be ideal, as it is conceivable that chemokine expression might require some day to reach optimal levels. Therefore, it is possible that injecting chemokines in a time course study, prior to antigen injection, may induce higher antibody production as compared to antigen alone. Finally, it is also possible that chemokine need to be directly linked to antigens in order for chemokines to achieve their potential as adjuvants. Biragyn et al have shown that DNA vaccines encoding for chemokine-antigen fusion proteins are markedly more immunogenic than simple coinjection [11] and [12].

When gp160 was used as the immunogen, alone or with the chemokines, a high titer of antibodies of the subtype IgG2a was detected, while the IgG1-isotype was undetectable. This is consistent with a Th1-polarized response, which might be related to the mode by which this membrane-bound protein is presented to the immune system. In contrast, it was observed the IgG1/IgG2A-isotype ratio skewed towards IgG1 in all groups receiving the secreted gp120-protein expression construct, consistent with a Th2 bias of the induced immune response. When antigen-induced proliferative responses were measured that are associated with helper response a robust proliferation in response to the gp120 antigen was observed while, surprisingly, HIV-$1_{BaL}$gp160 did not stimulate antigen-specific proliferation of $CD4^+T$ cells. (data not shown). This likely was due to the toxicity of gp160 [31].

It was observed that induced IFN-γ levels were notably higher in animals receiving gp160, with or without chemokine, as compared to all groups given gp120. An assessment of IFN-γ producing cells by ELISpot using restimulated splenocytes taken 6 weeks after the final immunization revealed that vaccination with gp160 induced a higher number of antigen-specific IFN-γ-secreting cells than the soluble antigen gp120. Furthermore, co-injection of chemokines with gp120 failed to enhance the IFN-γ production to levels attained with gp160 alone. These data suggest that the gp160-expressing construct induced a Th1-polarized response, while the gp120-expressing construct induced a Th2-polarized response, which is consistent with their mode of antigen presentation.

Taken together, three lines of evidence indicate that it was possible to selectively modulate immune responses to the HIV antigens by co-administration of certain chemokines. First, the co-administration of envelope DNA with BLC DNA elicited responses of the Th2-phenotype. The immunization protocol did not yield increased total antibody titers, and was even associated with lower titers of anti-gp160 antibody versus inoculation with envelope alone at the end of the 10-week study. However, when the BLC expression construct was co-administered with gp120, lower titers of IgG2a anti-envelope antibodies were observed as compared to the antigen alone group. Further, BLC co-injection caused reduced levels of secreted IFN-γ as compared to injection with gp160 alone as shown in FIG. 4B, which is also consistent with the induction of a Th2-phenotype. In apparent contrast, co-injection of BLC and gp120 elicited higher levels of secreted IFN-γ versus injection of gp120 alone, but in this group the baseline production of IFN-γ was much lower compared to that observed with gp160. It was found that BLC increased the number of IFN-γ-producing cells independently of the co-injected antigen, suggesting a complex mode of action for this chemokine.

Second, MCP-1 expression plasmids co-injected with gp120 DNA appeared to elicit a Th1-type of immune response. This protocol did not affect antibody production, while there was a decrease in total antibody titers in conjunction with gp160, similar to that observed in the case of BLC. MCP-1 reduced the IgG2a/IgG1 ratio in the gp160-injected group, as compared to the gp160 only group, while in the gp120 immunization group MCP-1 did not alter this ratio. Similar suppression was observed with the gp160 DNA antigens in the presence of RANTES, suggesting that the effect is not antigen-dependent (see below). MCP-1 co-injection was associated with high levels of IFN-γ production from cells, with the highest stimulated versus background signal for all immunization groups, regardless of which antigen was used. IFN-γ ELISpot assays on restimulated splenocytes collected 6 weeks after the final immunization revealed that MCP-1 co-injection significantly increased this parameter when co-injected with either gp120 or gp160, further strengthening evidence that this chemokine is associated with the induction of a Th1-type of immune response.

Third, RANTES appeared to suppress humoral responses to both gp120 and gp160, suggesting that the effect is not antigen-dependent. RANTES expression constructs co-injected with antigen induced a slight increase of IgG2a antibodies. Antigen-induced proliferation of splenocytes from animals immunized with gp120 co-administered with RANTES was also higher than that observed with cells taken from control animals receiving gp120 alone, again suggesting a bias toward Th1-type responses as shown in FIG. 3. The splenocytes from RANTES-co-injected animals also produced the highest absolute levels of IFN-γ production, independent of the co-injected antigen. As expected, IFN-γ levels were higher in conjunction with gp160, suggesting a synergistic effect on the IFN-γ production of the Th1-associated chemokine RANTES and gp160 antigen. IFN-γ ELISpot assays on restimulated splenocytes revealed that the number of IFN-Y secreting cells showed that RANTES produced a statistically significant increase in conjunction with gp160, but not with gp120 as shown in FIG. 5.

Thus, the present data emphasize that chemokines can be used to engineer the immune response to DNA vaccines by favoring the formation of either cellular or humoral protection, or both, hence shifting the Th profile of the immune response. Unbalanced Th responses have been observed in a variety of diseases, including AIDS, and this imbalance may impact on the effectiveness of vaccines, especially in populations of developing countries where infections, including HIV, are concomitant with parasitic diseases, which shift the immune response towards a Th2 profile [32] and [33]. Thus, vaccine protocols in these contexts may face the challenge of "redirecting" immune responses [32] and future immunization protocols may be modified and "tailored" to elicit an immune response of a desired profile, regarded as most adequate to fight a pathogen or a neoplastic cell, or to "redirect" immune response in a particular immunologic background, as in the case of parasite-infested areas with Th2-skewed immunity.

REFERENCES

The contents of all references, patents or patent applications cited herein are hereby incorporated by reference herein for all purposes.

[1] P. H. Naylor and J. W. Hadden, T cell targeted immune enhancement yields effective T cell adjuvants, *Int. Immunopharmacol.* 3 (2003) (8), pp. 1205-1215.

[2] S. M. Santini and F. Belardelli, Advances in the use of dendritic cells and new adjuvants for the development of therapeutic vaccines, *Stem. Cells* 21 (2003) (4), pp. 495-505.

[3] J. D. Boyer, M. Chattergoon and K. Muthumani et al., Next generation DNA vaccines for HIV-1, *J. Liposome Res.* 12 (2002) (1-2), pp. 137-142.

[4] F. Sallusto, A. Lanzavecchia and C. R. Mackay, Chemokines and chemokine receptors in T-cell priming and Th1/Th2-mediated responses, *Immunol. Today* 19 (1998) (12), pp. 568-574.

[5] V. Appay and S. L. Rowland-Jones, RANTES: a versatile and controversial chemokine, *Trends Immunol.* 22 (2001) (2), pp. 83-87.

[6] W. J. Karpus and K. J. Kennedy, MIP-1alpha and MCP-1 differentially regulate acute and relapsing autoimmune encephalomyelitis as well as Th1/Th2 lymphocyte differentiation, *J. Leukoc. Biol.* 62 (1997) (5), pp. 681-687.

[7] W. W. Leitner, H. Ying and N. P. Restifo, DNA and RNA-based vaccines: principles, progress and prospects, *Vaccine* 18 (1999) (9-10), pp. 765-777.

[8] K. Q. Xin, Y. Lu and K. Hamajima et al., Inmunization of RANTES expression plasmid with a DNA vaccine enhances HIV-1-specific immunity, *Clin. Immunol.* 92 (1999) (1), pp. 90-96.

[9] J. J. Kim, J. S. Yang, T. Dentchev, K. Dang and D. B. Weiner, Chemokine gene adjuvants can modulate immune responses induced by DNA vaccines, *J. Interferon Cytokine Res.* 20 (2000) (5), pp. 487-498.

[10] Y. Manome, P. Y. Wen and A. Hershowitz et al., Monocyte chemoattractant protein-1 (MCP-1) gene transduction: an effective tumor vaccine strategy for non-intracranial tumors, *Cancer Immunol. Immunother.* 41 (1995) (4), pp. 227-235.

[11] A. Biragyn, I. M. Belyakov, Y. H. Chow, D. S. Dimitrov, J. A. Berzofsky and L. W. Kwak, DNA vaccines encoding human immunodeficiency virus-1 glycoprotein 120 fusions with proinflammatory chemoattractants induce systemic and mucosal immune responses, *Blood* 100 (2002) (4), pp. 1153-1159.

[12] A. Biragyn, K. Tani, M. C. Grimm, S. Weeks and L. W. Kwak, Genetic fusion of chemokines to a self tumor antigen induces protective, T-cell dependent antitumor immunity, *Nat. Biotechnol.* 17 (1999) (3), pp. 253-258.

[13] R. Forster, A. E. Mattis, E. Kremmer, E. Wolf, G. Brem and M. Lipp, A putative chemokine receptor, BLR1, directs B cell migration to defined lymphoid organs and specific anatomic compartments of the spleen, *Cell* 87 (1996) (6), pp. 1037-1047.

[14] T. R. Fouts, R. Tuskan and K. Godfrey et al., Expression and characterization of a single-chain polypeptide analogue of the human immunodeficiency virus type 1 gp120-CD4 receptor complex, *J. Virol.* 74 (2000) (24), pp. 11427-11436.

[15] Y. Miyahira, K. Murata and D. Rodriguez et al., Quantification of antigen specific CD8+T cells using an ELISPOT assay, *J. Immunol. Methods* 181 (1995) (1), pp. 45-54.

[16] K. Yang, S. Wang and K. S. Chang et al., Immune responses and protection obtained with rotavirus VP6 DNA vaccines given by intramuscular injection, *Vaccine* 19 (2001) (23-24), pp. 3285-3291.

[17] J. D. Ahlers, N. Dunlop, D. W. Ailing, P. L. Nara and J. A. Berzofsky, Cytokine-in-adjuvant steering of the immune response phenotype to HIV-1 vaccine constructs: granulocyte-macrophage colony-stimulating factor and TNF-alpha synergize with IL-12 to enhance induction of cytotoxic T lymphocytes, *J. Immunol.* 158 (1997) (8), pp. 3947-3958.

[18] D. D. Taub, J. R. Ortaldo, S. M. Turcovski-Corrales, M. L. Key, D. L. Longo and W. J. Murphy, Beta chemokines costimulate lymphocyte cytolysis, proliferation, and lymphokine production, *J. Leukoc. Biol.* 59 (1996) (1), pp. 81-89.

[19] B. Spellberg and J. E. Edwards Jr., Type 1/type 2 immunity in infectious diseases, *Clin. Infect. Dis.* 32 (2001) (1), pp. 76-102.

[20] K. Song, Y. Chang and G. J. Prud'homme, Regulation of T-helper-1 versus T-helper-2 activity and enhancement of tumor immunity by combined DNA-based vaccination and nonviral cytokine gene transfer, *Gene Ther.* 7 (2000) (6), pp. 481-492.

[21] P. R. Hutchings, G. Cambridge, J. P. Tite, T. Meager and A. Cooke, The detection and enumeration of cytokine-secreting cells in mice and man and the clinical application of these assays, *J. Immunol. Methods* 120 (1989) (1), pp. 1-8.

[22] D. I. Stott, Immunoblotting, dot-blotting, and ELISPOT assays: methods and applications, *J. Immunoassay* 21 (2000) (2-3), pp. 273-296.

[23] J. F. Bach, Cytokine-based immunomodulation of autoimmune diseases: an overview, *Transplant. Proc.* 28 (1996) (6), pp. 3023-3025.

[24] D. M. Pardoll, Paracrine cytokine adjuvants in cancer immunotherapy, *Annu. Rev. Immunol.* 13 (1995), pp. 399-415.

[25] S. Gurunathan, D. M. Klinman and R. A. Seder, DNA vaccines: immunology, application, and optimization, *Annu. Rev. Immunol.* 18 (2000), pp. 927-974.

[26] B. Moser and P. Loetscher, Lymphocyte traffic control by chemokines, *Nat. Immunol.* 2 (2001) (2), pp. 123-128.

[27] D. Behringer, V. Kresin, R. Henschler, R. Mertelsmann and A. Lindemann, Cytokine and chemokine production by CD34+ haemopoietic progenitor cells: detection in single cells, *Br. J. Haematol.* 97 (1997) (1), pp. 9-14.

[28] G. Deliyannis, J. S. Boyle, J. L. Brady, L. E. Brown and A. M. Lew, A fusion DNA vaccine that targets antigen-presenting cells increases protection from viral challenge, *Proc. Natl. Acad. Sci. U.S.A.* 97 (2000) (12), pp. 6676-6680.

[29] M. Corr, A. von Damm, D. J. Lee and H. Tighe, In vivo priming by DNA injection occurs predominantly by antigen transfer, *J. Immunol.* 163 (1999) (9), pp. 4721-4727.

[30] D. R. Drew, M. Lightowlers and R. A. Strugnell, Humoral immune responses to DNA vaccines expressing secreted, membrane bound and non-secreted forms of the Tania ovis 45W antigen, *Vaccine* 18 (2000) (23), pp. 2522-2532.

[31] X. Pang, M. Zhang and A. I. Dayton, Development of dengue virus replicons expressing HIV-1 gp120 and other heterologous genes: a potential future tool for dual vaccination against dengue virus and HIV, *BMC Microbiol.* 1 (2001) (1), p. 28.

[32] M. Ayash-Rashkovsky, Z. Weisman, S. Zlotnikov, E. Raz, Z. Bentwich and G. Borkow, Induction of antigen-specific Th1-biased immune responses by plasmid DNA in schistosoma-infected mice with a preexistent dominant Th2 immune profile, *Biochem. Biophys. Res. Commun.* 282 (2001) (5), pp. 1169-1176.

[33] M. Ayash-Rashkovsky, Z. Weisman, J. Diveley, R. B. Moss, Z. Bentwich and G. Borkow, Generation of Th1 immune responses to inactivated, gp120-depleted HIV-1 in mice with a dominant Th2 biased immune profile via immunostimulatory [correction of imunostimulatory] oligonucleotides-relevance to AIDS vaccines in developing countries, *Vaccine* 20 (2002) (21-22), pp. 2684-2692.

[34] J. J. Kim, J. S. Yang, L. Montaner, D. J. Lee, A. A. Chalian and D. B. Weiner, Coimmunization with IFN-gamma or IL-2, but not IL-13 or IL-4 cDNA can enhance Th1-type DNA vaccine-induced immune responses in vivo, *J. Interferon Cytokine Res.* 20 (2000) (3), pp. 311-319.

[35] B. J. Rollins, JE/MCP-1: an early-response gene encodes a monocyte-specific cytokine, *Cancer Cells* 3 (1991) (12), pp. 517-524.

[36] D. R. Huang, J. Wang, P. Kivisakk, B. J. Rollins and R. M. Ransohoff, Absence of monocyte chemoattractant protein 1 in mice leads to decreased local macrophage recruitment and antigen-specific T helper cell type 1 immune response in experimental autoimmune encephalomyelitis, *J. Exp. Med.* 193 (2001) (6), pp. 713-726.

[37] J. T. Siveke and A. Hamann, T helper 1 and T helper 2 cells respond differentially to chemokines, *J. Immunol.* 160 (1998) (2), pp. 550-554.

[38] T. R. Traynor, A. C. Herring, M. E. Dorf, W. A. Kuziel, G. B. Toews and G. B. Huffnagle, Differential roles of CC chemokine ligand 2/monocyte chemotactic protein-1 and CCR2 in the development of T1 immunity, *J. Immunol.* 168 (2002) (9), pp. 4659-4666.

That which is claimed:

1. A method for directing a Th-1 type immune response to an antigen, the method comprising:

administering to a subject a first component comprising an HIV envelope antigen against which an immune response is desired in the subject; and administering a second component comprising RANTES, wherein the first component and second component are administered in an effective amount to produce an immune response.

2. The method according to claim 1, wherein the second component is administered with the first component concurrently, before administration of the first component, or after.

3. The method according to claim 1, wherein the first component is gp120 or gp160.

4. The method according to claim 1, wherein a single nucleic acid encodes for both the first component and the second component.

5. A method for inducing and directing a cellular immune response in a subject in need thereof, the method comprising administering to the subject an HIV envelope antigen and RANTES, wherein the HIV envelope antigen is gp 120.

6. A method for biasing an immune response towards an HIV gp 120 envelope antigen, the method comprising introducing an HIV envelope antigen and a RANTES chemokine to a subject; and measuring immune response, wherein the RANTES chemokine selectively recruits specific cell subsets to bias the immune responses towards a Th1 response.

7. The method according to claim 6, wherein in the combination of gp120 and RANTES increases the level of production of IgG2 antibodies.

8. A method for increasing levels of a Th1 immune response, the method comprising:

a) administering a first component comprising an HIV envelope antigen against which an immune response is desired in a subject;

b) administering a second component comprising RANTES of said chemokine wherein the first component and second component are administered in an effective amount to increase level of a Th1 immune response.

9. The method according to claim 8, wherein the antigen is gp120 or gp160.

10. The method of claim 1, wherein the administering to the subject an HIV envelope antigen and RANTES is in the form of nucleic acid encoding such proteins.

* * * * *